United States Patent
Tsukizawa

(10) Patent No.: US 8,406,479 B2
(45) Date of Patent: Mar. 26, 2013

(54) VISUAL AXIS DIRECTION DETECTION DEVICE AND VISUAL LINE DIRECTION DETECTION METHOD

(75) Inventor: Sotaro Tsukizawa, Tokyo (JP)

(73) Assignee: Panasonic Corporation, Osaka (JP)

( * ) Notice: Subject to any disclaimer, the term of this patent is extended or adjusted under 35 U.S.C. 154(b) by 1094 days.

(21) Appl. No.: 12/373,582

(22) PCT Filed: Jul. 13, 2007

(86) PCT No.: PCT/JP2007/064011
§ 371 (c)(1),
(2), (4) Date: Jan. 13, 2009

(87) PCT Pub. No.: WO2008/007781
PCT Pub. Date: Jan. 17, 2008

(65) Prior Publication Data
US 2009/0304232 A1    Dec. 10, 2009

(30) Foreign Application Priority Data
Jul. 14, 2006    (JP) .................................. 2006-194892

(51) Int. Cl.
*G06K 9/00*    (2006.01)
*G05B 19/00*    (2006.01)

(52) U.S. Cl. ....................... 382/115; 382/118; 340/5.83

(58) Field of Classification Search .................. 382/103, 382/104, 117, 118, 164, 165, 199, 288; 348/77, 348/78, 222.1; 351/210, 222, 211, 212; 706/15, 706/17, 20
See application file for complete search history.

(56) References Cited

U.S. PATENT DOCUMENTS
5,629,752 A * 5/1997 Kinjo .............................. 355/35
(Continued)

FOREIGN PATENT DOCUMENTS
JP    2-224637    9/1990
JP    2-224637 A    9/1990
(Continued)

OTHER PUBLICATIONS

Erik Pogalin, Andre Redert, Ioannis Patras, Emile A. Hendriks, Gaze Tracking by sing Factorized Likelihoods Particle Filtering and Stereo Vision, Proceedings of the Third International Symposium on 3D Data Processing, Visualization, and Transmission (3DPVT'06), p. 57-64, Jun. 14-16, 2006.*

(Continued)

*Primary Examiner* — Andrae S Allison
(74) *Attorney, Agent, or Firm* — Greenblum & Bernstein, P.L.C.

(57) ABSTRACT

Provided is a visual axis direction detection device capable of obtaining a highly accurate visual axis direction detection result without performing a particular calibration for each of examinees. The device (100) includes: a feature calculation unit (160) which calculates as a reference position, a 3D position of the center of a face of an examinee whose visual axis direction is to be detected, from a 3D position of two face parts positioned symmetrically, and calculates as a feature position, a 3D position of the center of the right and left pupils of the examinee in the horizontal direction; a visual axis direction feature amount calculation unit (172) for calculating a shift amount of the feature position from the reference position in the horizontal direction as a visual axis direction feature amount; and a visual axis vector calculation unit (173) for calculating the visual axis direction of the examinee according to the visual axis direction feature amount.

5 Claims, 20 Drawing Sheets

U.S. PATENT DOCUMENTS

| | | | |
|---|---|---|---|
| 5,859,921 A * | 1/1999 | Suzuki | 382/118 |
| 6,055,323 A * | 4/2000 | Okumura | 382/118 |
| 6,707,933 B1 * | 3/2004 | Mariani et al. | 382/118 |
| 7,003,139 B2 * | 2/2006 | Endrikhovski et al. | 382/118 |
| 2003/0098954 A1 | 5/2003 | Amir et al. | |
| 2005/0175218 A1 | 8/2005 | Vertegaal et al. | |
| 2009/0273687 A1 * | 11/2009 | Tsukizawa et al. | 348/222.1 |

FOREIGN PATENT DOCUMENTS

| | | |
|---|---|---|
| JP | 2003-015816 | 1/2003 |
| JP | 2003-015816 A | 1/2003 |
| JP | 2003-070742 | 3/2003 |
| JP | 2003-070742 A | 3/2003 |
| JP | 2004-255074 | 9/2004 |
| JP | 2004-255074 A | 9/2004 |
| WO | 2005/046465 | 5/2005 |

OTHER PUBLICATIONS

International Search Report in PCT/JP2007/064011, dated Oct. 23, 2007.

English language Abstract of JP 2003-015816 A (Jan. 17, 2003).

English language Abstract of JP 2004-255074 A (Sep. 16, 2004).

* cited by examiner

| FACE DIRECTION | EYE TO BE USED |
|---|---|
| LEFT DIRECTION | RIGHT EYE |
| RIGHT DIRECTION | LEFT EYE |

| HORIZONTAL FACE DIRECTION ANGLE[°] | LEFT EYE WEIGHT COEFFICIENT | HORIZONTAL FACE DIRECTION ANGLE[°] | LEFT EYE WEIGHT COEFFICIENT | HORIZONTAL FACE DIRECTION ANGLE[°] | LEFT EYE WEIGHT COEFFICIENT | HORIZONTAL FACE DIRECTION ANGLE[°] | LEFT EYE WEIGHT COEFFICIENT |
|---|---|---|---|---|---|---|---|
| -40 | 1 | -20 | 0.75 | 0 | 0.5 | 20 | 0.25 |
| -39 | 1 | -19 | 0.725 | 1 | 0.5 | 21 | 0.225 |
| -38 | 1 | -18 | 0.7 | 2 | 0.5 | 22 | 0.2 |
| -37 | 1 | -17 | 0.675 | 3 | 0.5 | 23 | 0.175 |
| -36 | 1 | -16 | 0.65 | 4 | 0.5 | 24 | 0.15 |
| -35 | 1 | -15 | 0.625 | 5 | 0.5 | 25 | 0.125 |
| -34 | 1 | -14 | 0.6 | 6 | 0.5 | 26 | 0.1 |
| -33 | 1 | -13 | 0.575 | 7 | 0.5 | 27 | 0.075 |
| -32 | 1 | -12 | 0.55 | 8 | 0.5 | 28 | 0.05 |
| -31 | 1 | -11 | 0.525 | 9 | 0.5 | 29 | 0.025 |
| -30 | 1 | -10 | 0.5 | 10 | 0.5 | 30 | 0 |
| -29 | 0.975 | -9 | 0.5 | 11 | 0.475 | 31 | 0 |
| -28 | 0.95 | -8 | 0.5 | 12 | 0.45 | 32 | 0 |
| -27 | 0.925 | -7 | 0.5 | 13 | 0.425 | 33 | 0 |
| -26 | 0.9 | -6 | 0.5 | 14 | 0.4 | 34 | 0 |
| -25 | 0.875 | -5 | 0.5 | 15 | 0.375 | 35 | 0 |
| -24 | 0.85 | -4 | 0.5 | 16 | 0.35 | 36 | 0 |
| -23 | 0.825 | -3 | 0.5 | 17 | 0.325 | 37 | 0 |
| -22 | 0.8 | -2 | 0.5 | 18 | 0.3 | 38 | 0 |
| -21 | 0.775 | -1 | 0.5 | 19 | 0.275 | 39 | 0 |

VISUAL AXIS DIRECTION DETECTION DEVICE AND VISUAL LINE DIRECTION DETECTION METHOD

TECHNICAL FIELD

The present invention relates to a gaze direction detecting apparatus and gaze direction detecting method for detecting the direction of a person's gaze.

BACKGROUND ART

In recent years, specifying what a person pays attention to or thinks by measuring the direction of the person's gaze, has gained popularity in many fields. Techniques of non-contact detection of the direction of a person's gaze have been proposed in the past (see, for example, Patent Document 1 and Patent Document 2).

The gaze recognition apparatus disclosed in Patent Document 1 photographs an image of a person who is the target of gaze direction detection (hereinafter "subject") using a stereo camera, analyzes the photographed image and detects the three dimensional positions of the center of the pupil, the inner corner and the outer corner of one eye. Next, presuming that the inner and outer corners of the eye are located on the spherical exterior of the eyeball, the gaze recognition apparatus specifies the three dimensional position of the center of the subject's eyeball based on the position of the inner corner of the eye, the position of the outer corner of the eye and the radius of the eyeball. Further, the gaze recognition apparatus calculates a vector starting from the center of the eyeball and ending at the center of the pupil, as a vector to indicate the direction of the subject's gaze.

Further, the gaze direction detecting apparatus disclosed in Patent Document 2 analyzes an image of the subject photographed by a stereo cameras and calculates the three dimensional positions of the center of the subject's pupil and the plane where the contour of the subject's pupil passes. Further, the gaze direction detecting apparatus detects the direction where the normal passes the center of the pupil amongst the normals passing the plane where the contour of the pupil passes, as the direction of the subject's gaze.

Patent Document 1: Japanese Patent Application Laid-open No. 2003-15816
Patent Document 2: Japanese Patent Application Laid-open No. 2004-255074

DISCLOSURE OF INVENTION

Problem to be Solved by the Invention

However, the shape and visual features of the inner and outer corners of the eye vary significantly between individuals. Therefore, to acquire an accurate gaze direction detection result, the apparatus disclosed in above Patent document 1 needs to specify the relationships between the actual gaze direction and the inner and outer corners of the eye by measurement on a per subject basis, and correct various parameters for use in the calculation of the gaze direction. That is, the apparatus needs to be calibrated on a per subject basis (i.e. calibration), and, consequently, a problem arises that much processing is required and furthermore the apparatus is made complicated.

Further, the conditions of the contour of the pupil that is detected visually vary significantly between individuals, depending on the conditions of the eyelashes and eyelids and whether or not glasses or contact lenses are worn. Consequently, like the apparatus disclosed in Patent Document 1, the apparatus disclosed in above Patent Document 2 needs also to be calibrated on a per subject basis to acquire an accurate gaze direction detection result.

It is therefore an object of the present invention to provide a gaze direction detecting apparatus and gaze direction detecting method for acquiring an accurate gaze direction detection result without having to perform calibration on a per subject basis.

Means for Solving the Problem

The gaze direction detecting apparatus of the present invention employs a configuration having: a reference position calculating section that calculates a three dimensional position of a center of a face of a subject targeted for a gaze direction detection as a reference position, from three dimensional positions of two face parts that are located symmetrically in lateral direction; a feature position calculating section that calculates three dimensional position of a lateral center of centers of right and left pupils of the subject as a feature position, from three dimensional positions of the centers of the right and left pupils; a gaze direction feature measure calculating section that calculates a degree of deviation of the feature position with respect to the reference position in the lateral direction, as a gaze direction feature measure; and a gaze direction calculating section that calculates a direction of the subject's gaze based on the gaze direction feature measure.

The gaze direction detecting method of the present invention employs the steps including: a feature calculating step of calculating a three dimensional position of a center of a face of a subject targeted for a gaze direction detection as a reference position, from three dimensional positions of two face parts that are located symmetrically in lateral direction, and calculating three dimensional positions of a lateral center of centers of right and left pupils of the subject as a feature position, from three dimensional positions of the centers of right and left pupils; a gaze direction feature measure calculating step of calculating a degree of deviation of the feature position with respect to the reference position in the lateral direction, as a gaze direction feature measure; and a gaze direction calculating step of calculating a direction of the subject's gaze based on the gaze direction feature measure.

Advantageous Effect of the Invention

According to the present invention, it is possible to detect the direction of a person's gaze from parameters that can be acquired accurately and that vary little between individuals, such as the three dimensional positions of the centers of the right and left pupils and the three dimensional positions of two face parts that are located laterally symmetrically such as the inner corners of the eyes. That is, it is possible to acquire an accurate gaze direction detection result without having to perform calibration on a per subject basis.

BRIEF DESCRIPTION OF DRAWINGS

FIG. 15 illustrates an example of contents of a selection information table according to Embodiment 5 of the present invention;

FIG. 18 illustrates an example of content of weight information according to Embodiment 6 of the present invention;

BEST MODE FOR CARRYING OUT THE INVENTION

Embodiments of the present invention will be explained below in detail with reference to the accompanying drawings.
(Embodiment 1)

Figure 1:
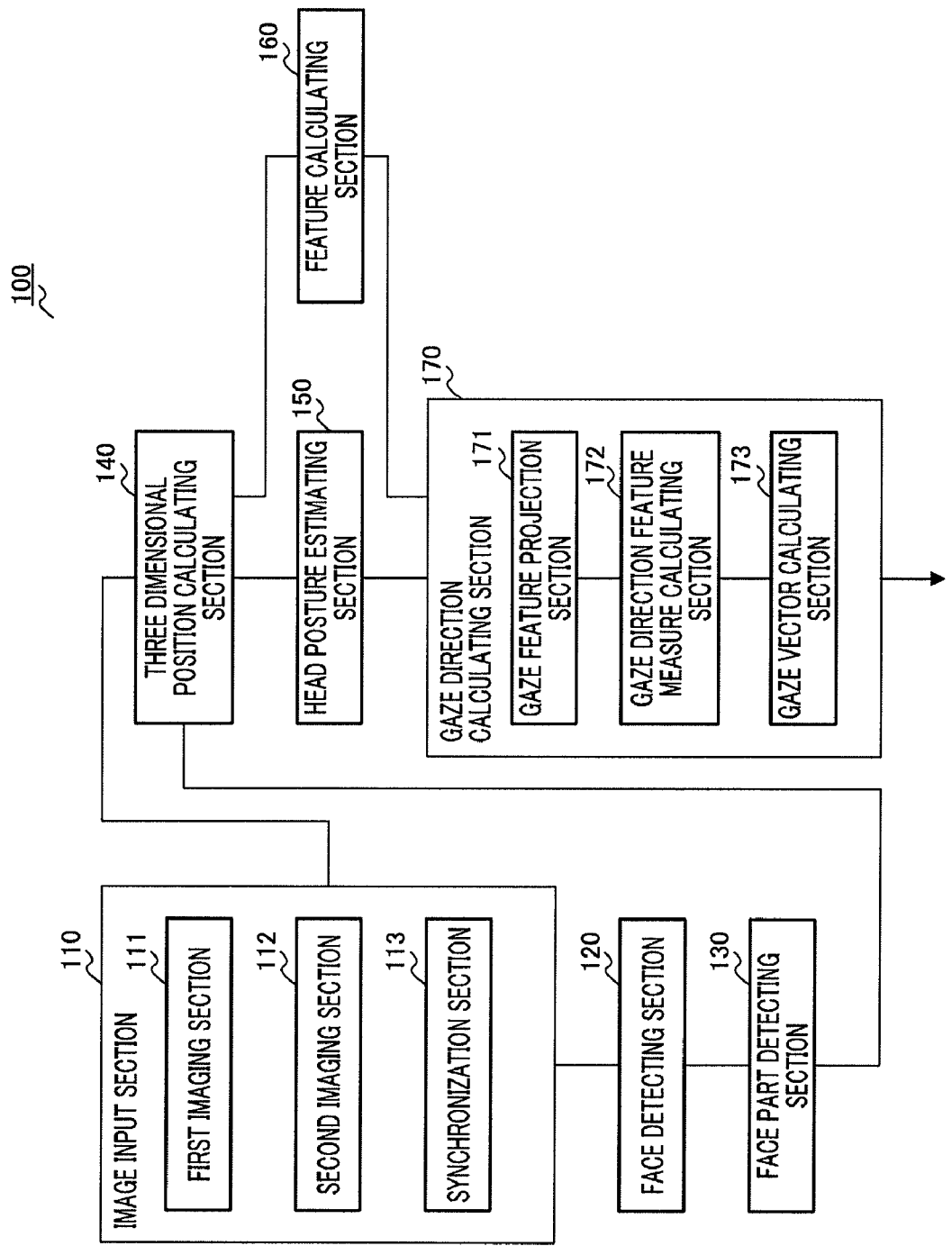
FIG. 1 is a block diagram showing the configuration of a gaze direction detecting apparatus according to Embodiment 1 of the present invention.

FIG. 1 is a block diagram showing the configuration of a gaze direction detecting apparatus according to Embodiment 1 of the present invention. Gaze direction detecting apparatus 100 of the present embodiment is, for example, an apparatus that is equipped with a warning apparatus to warn the driver of the risk of accidents by inattentive driving or the like and that detects the direction of the driver's gaze. Here, the detection of the gaze direction refers to detecting a vector of the same orientation (hereinafter "gaze vector") as the vector starting from the subject's eye and ending at the target the subject looks at.

In FIG. 1, gaze direction detecting apparatus 100 is configured with image input section 110, face detecting section 120, face part detecting section 130, three dimensional position calculating section 140, head posture estimating section 150, feature calculating section 160 and gaze direction calculating section 170. Further, image input section 110 is configured with first imaging section 111, second imaging section 112 and synchronization section 113, and gaze direction calculating section 170 is configured with gaze feature projection section 171, gaze direction feature measure calculating section 172 and gaze vector calculating section 173.

Image input section 110 photographs and inputs an image of the subject, and outputs the input image to face detecting section 120 and three dimensional position calculating section 140.

In image input section 110, first imaging section 111 and second imaging section 112 each have an image sensor (not shown) and photograph images of the subject from different positions. The image sensor is configured with, for example, lenses and CCD (Charge Coupled Device) or CMOS (Complementary Metal Oxide Semiconductor). Further, the internal parameters to define the relationships between input images and the photographing positions of first imaging section 111 and second imaging section 112, and the external parameters to define the photographing positions of first imaging section 111 and second imaging section 112 are known. Here, for example, the internal parameters include the focal distance, image center coordinate, pixel size and lens distortion coefficient, and the external parameters include translation vector and rotation matrix. Further, synchronization section 113 controls first imaging section 111 and second synchronization section 112 to photograph images at synchronized timing. That is, image input section 110 functions as a stereo camera and outputs a pair of two images (hereinafter "stereo image pair") taken virtually at the same time in first imaging section 111 and second imaging section 112. Further, in a case where the above-noted CCD or CMOS is used as the image sensor, image input section 110 functions as a digital stereo camera.

Face detecting section 120 detects the region of the image of the subject's face (hereinafter "face") from the image inputted from image input section 110, and outputs face region information indicating the region of the face image (hereinafter "face region") with the image from which the face region is detected in the stereo image pair, to face part detecting section 130.

Face part detecting section 130 detects parts that are located laterally symmetrically in the face with reference to the center of the face (hereinafter "face parts"), from the image inputted from face detecting section 120, based on the face region information inputted from face detecting section 120. That is, face part detecting section 130 detects images matching the face parts. For example, these face parts include the inner and outer corners of the eye, the nostrils, the corners of the mouth, and the inner and outer ends of the eyebrow. Further, face part detecting section 130 detects the centers of the right and left pupils of the subject (i.e. images matching the pupil centers) from the detected face parts (i.e., images matching the face parts). Further, face part detecting section 130 outputs face part two dimensional position information indicating the two dimensional positions of the detected face parts and pupil centers in the image in which the face region was detected, to three dimensional position calculating section 140.

Three dimensional position calculating section 140 calculates the three dimensional positions of the face parts based on the stereo image pair inputted from image input section 110, the face part two dimensional position information inputted from face part detecting section 130 and the known internal parameters and external parameters of above image input section 110. Further, three dimensional position calculating section 140 outputs face part three dimensional position information indicating the three dimensional positions of the face parts to head posture estimating section 150 and feature calculating section 160.

Head posture estimating section (i.e., head direction estimating section) 150 acquires from the face part three dimensional position information inputted from three dimensional position calculating section 140, a vector indicating the direction of the face front (hereinafter "face front vector") as a head posture parameter indicating the posture of the subject's head (hereinafter simply "head"). To be more specific, head posture estimating section 150 calculates a plane passing the three dimensional positions of more than three face parts including two face parts that are located laterally symmetrically, and acquires a normal vector of the plane as a head posture parameter. Further, head posture estimating section 150 outputs the acquired head posture parameter to gaze direction calculating section 170.

Feature calculating section 160 acquires a gaze feature parameter indicating a feature of the subject's gaze (hereinafter simply "gaze"), from the face part three dimensional position information inputted from three dimensional position calculating section 140. The gaze feature parameter is comprised of the three dimensional position of the gaze direction feature point, which moves depending on the gaze direction (i.e., feature position) and the three dimensional position of the gaze direction reference point which serves as a reference upon determining the movement of the gaze direction feature point (i.e., reference position). To be more specific, the gaze direction feature point is the middle point between the centers of the right and left pupils, and the gaze direction reference point is the middle point between two face parts that are located laterally symmetrically (i.e., the inner and outer corners of the right and left eyes). Further, feature calculating section 160 outputs the acquired gaze direction feature parameter in addition to the face part three dimensional position information, to gaze direction calculating section 170.

Gaze direction calculating section 170 calculates the gaze vector based on the head posture parameter inputted from head posture estimating section 150 and the gaze feature parameter and face part three dimensional position information inputted from feature calculating section 160.

In gaze direction calculating section 170, gaze feature projection section 171 calculates the three dimensional position of the gaze feature projection point acquired by projecting the gaze direction feature point vertically on the straight line passing two face parts that are located symmetrically and that derive the gaze direction reference point. Gaze direction feature measure calculating section 172 calculates the degree of deviation of the gaze direction reference point from the gaze feature projection point, as a measure to indicate the feature of the gaze direction (hereinafter "gaze direction feature measure"). Gaze vector calculating section 173 calculates the gaze vector based on the gaze direction feature measure and the face front vector. Gaze direction calculating section 170 outputs the calculated gaze vector, as the gaze direction detection result, to the above warning apparatus, for example.

Gaze direction detecting apparatus 100 contains CPU (Central Processing Unit), ROM (Read Only Memory) that stores control program, and RAM (Random Access Memory) as the working memory of CPU (not shown). That is, the functions of the sections of above gaze direction detecting apparatus 100 are implemented by making CPU execute the control program.

The operations of gaze direction detecting apparatus 100 employing the above-noted configuration will be explained below in detail.

Figure 2:
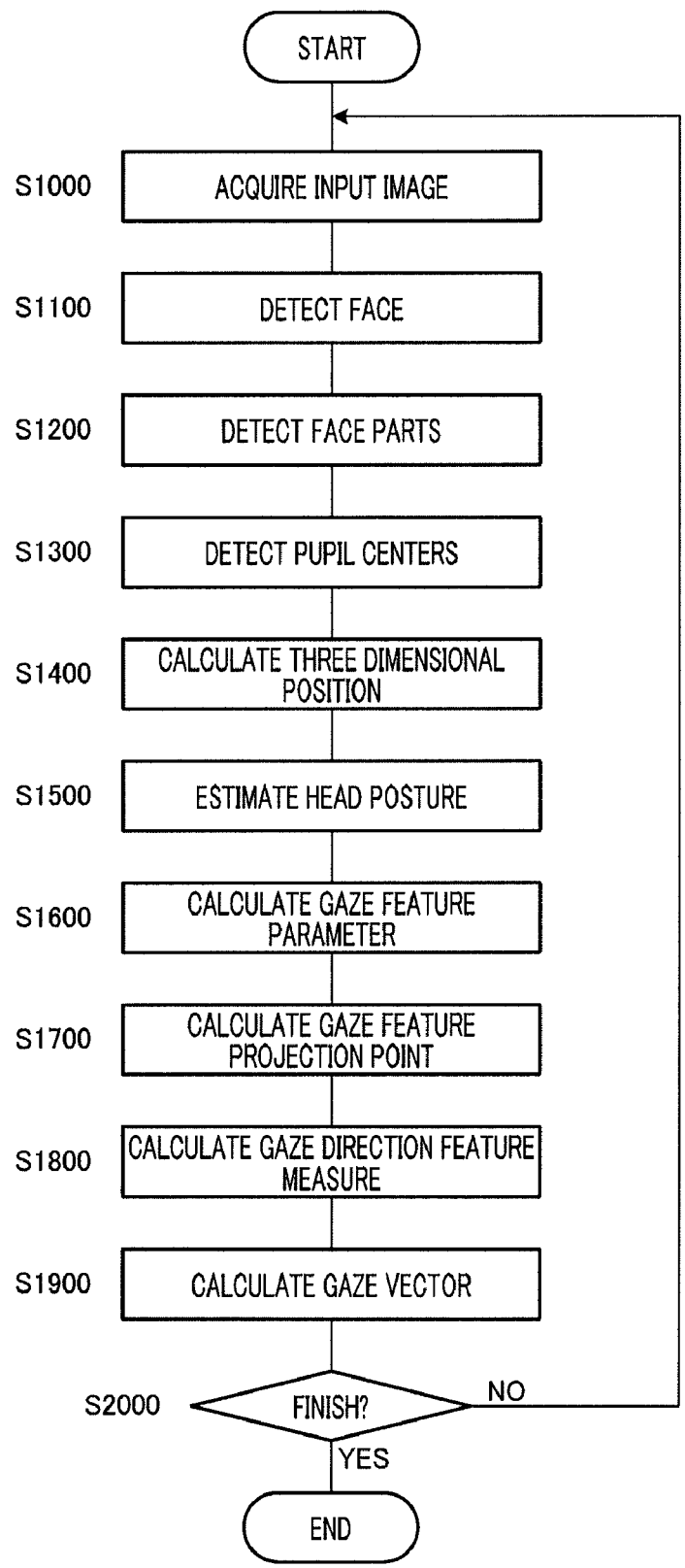
FIG. 2 is a flowchart showing the flow of gaze direction detection processing in a gaze direction detecting apparatus according to Embodiment 1 of the present invention.

FIG. 2 is a flowchart showing the flow of gaze direction detection processing in gaze direction detecting apparatus 100. This gaze direction detection processing is started when triggered by, for example, an input of a signal commanding a start of the above-noted warning apparatus and the designation of starting processing by user's operation.

In step S1000 in FIG. 2, image input section 110 inputs two images photographed in first imaging section 111 and second imaging section 112, as a stereo image pair.

Figure 3:
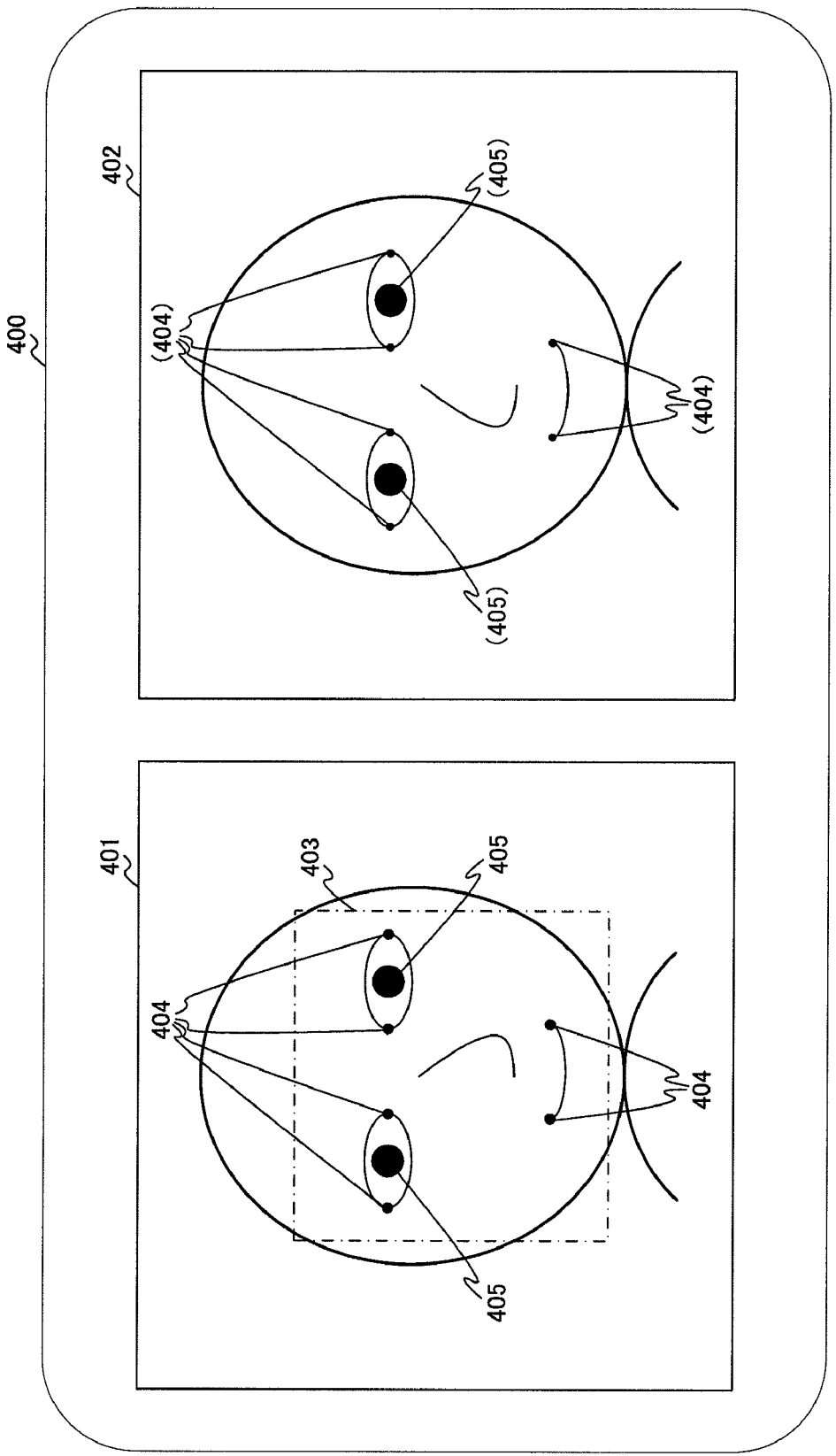
FIG. 3 illustrates an example of a stereo image pair acquired in an image input section according to Embodiment 1 of the present invention.

FIG. 3 illustrates an example of the stereo image pair acquired in image input section 110. As described above, stereo image pair 400 is comprised of image 401 photographed in first imaging section 111 (hereinafter "first image 401") and image 402 photographed in second imaging section 112 (hereinafter "second image 402"). Here, first imaging section 111 is positioned in a location to view the head slightly from the left side, and second imaging section 112 is positioned in a location to view the head slightly from the right side. Therefore, although first image 401 and second image 402 are photographed virtually at the same time under control of synchronization section 113, they still show different images.

As described above, when image input section 110 functions as a digital stereo camera, image input section 110 acquires first image 401 and second image 402 as image data of, for example, the PPM format (Portable Pix Map file format). Image input section 110 makes a storage section (not shown) (e.g., a predetermined memory space in the above RAM), which is equipped with image input section 110, store the acquired image data on a temporary basis. Further, face detecting section 120 and three dimensional position calculating section 140 acquire the image data of the PPM format from this storage section.

In step S1100 in FIG. 2, in stereo image pair 400 inputted in step S1000, face detecting section 120 detects face region 403 from first image 401 and generates the above-noted face region information. Here, face detecting section 120 may acquire only first image 401 from image input section 110.

Face detecting section 120 detects face region 403 by, for example, specifying from first image 401, the image part of the highest correlation with a feature image indicating the face region of an average face prepared in advance. To be more specific, face detecting section 120 extracts a plurality of characteristic image parts from first image 401, and compares the extracted image parts and a feature image. Further, face detecting section 120 determines from the extracted image parts, the image part having the highest similarity to the feature image as face region 403.

For example, face detecting section 120 may calculate the Gabor feature measure of first image 401, compares the calculated Gabor feature measure to the Gabor feature measure of the feature image prepared in advance, and use the inverse of the absolute value of the difference as the similarity. Here, the Gabor feature measure refers to the value indicating features of the image, calculated by performing the Gabor wavelet transform of the image.

Further, face detecting section 120 may detect the flesh color region or detect a region of a shape similar to an ellipse by analyzing first image 401, to detect face region 403 using the statistic pattern identification method. Here, if face region 403 can be detected in first image 401 and second image 402, it is obviously possible to adopt various other methods than the above.

Face parts are obviously located in the face. Therefore, by detecting face region 403 as described above, it is possible to limit the target region to search for face parts to the face region, thereby realizing high speed processing.

In step S1200, with face region 403 in first image 401 as the search region, face part detecting section 130 detects face parts 404 from first image 401, based on the face region information generated in step S1100. However, for example, face part detecting section 130 detects at least two types of face parts and detects both the right and left parts at least with respect to one type. For example, face part detecting section 130 detects the inner corners of the right and left eyes and the left corner of the mouth. Here, assume that, as face parts 404, the right and left corners of the mouth, the inner corners of the right and left eyes, and the outer corners of the right and left eyes are detected. As described above, these face parts 404 are located laterally symmetrically with reference to the center of the face.

For example, face part detecting section 130 detects face parts 404 by detecting the separability between locations in face region 403 in first image 401 by a separability filter and specifying parts matching face parts 404 amongst locations having high separability. To be more specific, face part detecting section 130 stores or learns in advance the location relationships between the face region and face parts, and detects locations of high likelihood amongst locations having high separability, as face parts 404. Further, face part detecting section 130 may detect face parts 403 by preparing a template of image parts created from image parts cut out from an image of an average face, performing template matching for all locations in face region 403 in first image 401 and searching for locations similar to the template.

In step S1300, with face region 403 in first image 401 as the search region, face part detecting section 130 detects pupil center 405 of the subject from first image 401, based on the face region information generated in step S1100.

For example, face part detecting section 130 adopts a circular separability filter for the region including the inner and outer corners of the eye in face parts 404, and detects the circle center where the degree of brightness is the highest, as pupil center 405. However, in this case, it is preferable to detect the eyelids by edge detection using the Sobel filter or by binarizing brightness using the Otsu threshold method, and use only the region between the top and bottom of the eyelids as the detection target range. Further, in the region including the inner and outer corners of the eye, face part detecting section 130 may calculate brightness sums in the horizontal direction and vertical direction, and use a point where both brightness sums are small, as pupil center 405. Here, if pupil center 405 can be detected, it is obviously possible to adopt various other methods than the above.

In step S1400, three dimensional calculating section 140 calculates the three dimensional positions of face parts 404 and pupil center 405 based on stereo image pair 400 acquired in step S1000, face parts 404 detected in step S1200 and pupil center 405 detected in step S1300. To be more specific, three dimensional calculating section 140 calculates the three dimensional positions of face parts 404 and pupil center 405 by a stereo method, based on the two dimensional positions of face parts 404 and pupil center 405 in first image 401 and second image 402, and on the internal parameters and external parameters of above-noted first imaging section 111 and second imaging section 112. Further, three dimensional position calculating section 140 outputs the calculated three dimensional positions of face parts, as face part three dimensional position information, to head posture estimating section 150 and feature calculating section 160.

For example, by performing template matching for second image 402, three dimensional position calculating section 140 detects points matching face parts 404 and pupil centers 405 in second image 402. To be more specific, three dimensional position calculating section 140 makes the image part including face parts 404 and the image part including pupil center 405 in first image 401 templates, and draws the epipolar lines of face parts 404 and pupil center 405 in first image 401, in second image 402. Further, on the epipolar lines, three dimensional position calculating section 140 searches for the points of the highest correlation with the matching template, and specifies the locations of the points in second image 402 matching face parts 404 and pupil center 405.

Here, three dimensional position calculating section 140 may create a three dimensional model of the face based on first image 401 and limit the search range for matching points in second image 402. Thus, by limiting the search region for the matching points of face parts 404 and pupil center 405, it is possible to realize high speed processing. Further, after creating a three dimensional model of the face shape, three dimensional position calculating section 140 preferentially searches for the matching points of face parts 405 of distinct features and then searches for the rest of the matching points not to cause contradiction in the three dimensional shape of the whole face. If the three dimensional positions of face parts 404 and pupil center 405 can be detected, it is obviously possible to adopt various other methods than the above.

In step S1500, head posture estimating section 150 estimates the posture of the head based on the three dimensional position of face parts 404 detected in step S1400, and acquires a head posture parameter.

For example, in face parts 404 acquired in step S1200, head posture estimating section 150 specifies a plane passing four points of the right and left corners of the mouth and the inner corners of the right and left eyes, and calculates the normal vector of the plane. In this case, the calculated normal vector is referred to as a face front vector, namely, the head posture parameter. However, in fact, it is difficult to find a plane passing all of the above four points regularly. Consequently, a plane in which the square sum of the lengths of the vertical lines drawn from the above points is minimized, is specified and the normal vector of the plane is made the face front vector. Further, for example, it is equally possible to specify a plane passing three points of the right and left corners of the mouth and the inner corner of one eye and make the normal vector of the plane as the face front vector. Further, it is equally possible to calculate a vector connecting the inner corners of the right and left eyes, and a vector connecting the inner corner of one eye and the middle point between the right and left corners of the mouth, and calculate the face front vector by calculating the exterior product of these two vectors. Further, as an evaluation method upon calculating a plane, it is equally possible to use robust estimation methods such as the M estimation. Here, if the face front vector can be calculated, it is obviously possible to adopt various other methods than the above.

In step S1600, feature calculating section 160 acquires a gaze feature parameter based on the three dimensional positions of pupil center 405 and face parts 404 detected in step S1400.

Feature calculating section 160 specifies the three dimensional position of the middle point between right and left pupil centers 405 from the three dimensional positions of right and left pupil centers 405, and uses the specified point as the above gaze direction feature point. Further, for example, feature calculating section 160 specifies the three dimensional position of the middle point between the right and left inner corners of the eyes from the three dimensional position of the right and left inner corners of the eyes in face parts 404, and uses the specified point as the above gaze direction reference point.

Further, it is equally possible to use the other middle point between face parts 404 that are located laterally symmetrically in the face, such as the middle point between the right and left outer corners of the eyes and the middle point between the right and left corners of the mouth, as the gaze direction reference point. Further, it is equally possible to select a plurality pairs of face parts that are located laterally symmetrically such as the right and left outer corners of the eyes and the right and left corners of the mouth, and use the median point of those face parts as the gaze direction reference point. That is, on conditions that the face is laterally symmetric, the gaze direction reference point is the center point of the face in the lateral direction. Feature calculating section 160 outputs to gaze direction calculating section 170, information about the three dimensional positions of face parts 404 deriving the gaze direction reference point in addition to the gaze feature parameter.

In step S1700, based on the gaze feature parameter and face part three dimensional position information acquired in step S1600, projection section 171 projects the gaze direction feature point to a straight line passing two face parts 404 that are located laterally symmetrically and that derive the gaze direction reference point, and acquires the projection point as the gaze feature projection point.

For example, when the gaze direction reference point is the middle point between the inner corners of the right and left eyes, gaze feature projection section 171 draws a vertical line from the gaze direction feature point to a straight line passing the right and left inner corners of the eyes, and acquires the intersection point of these lines as the gaze feature projection point. Further, for example, when the median point of more than three face parts 404 is made the gaze direction reference point, it is equally possible to divide face parts 404 in the right-half face and the left-half face and draw a vertical line to a line passing the median points of face parts 404 of the right-half face and left-half face.

In step S1800, gaze direction feature measure calculating section 172 calculates the gaze direction feature measure based on the gaze direction reference point acquired in step S1600 and the gaze feature projection point acquired in step S1700.

Figure 4:
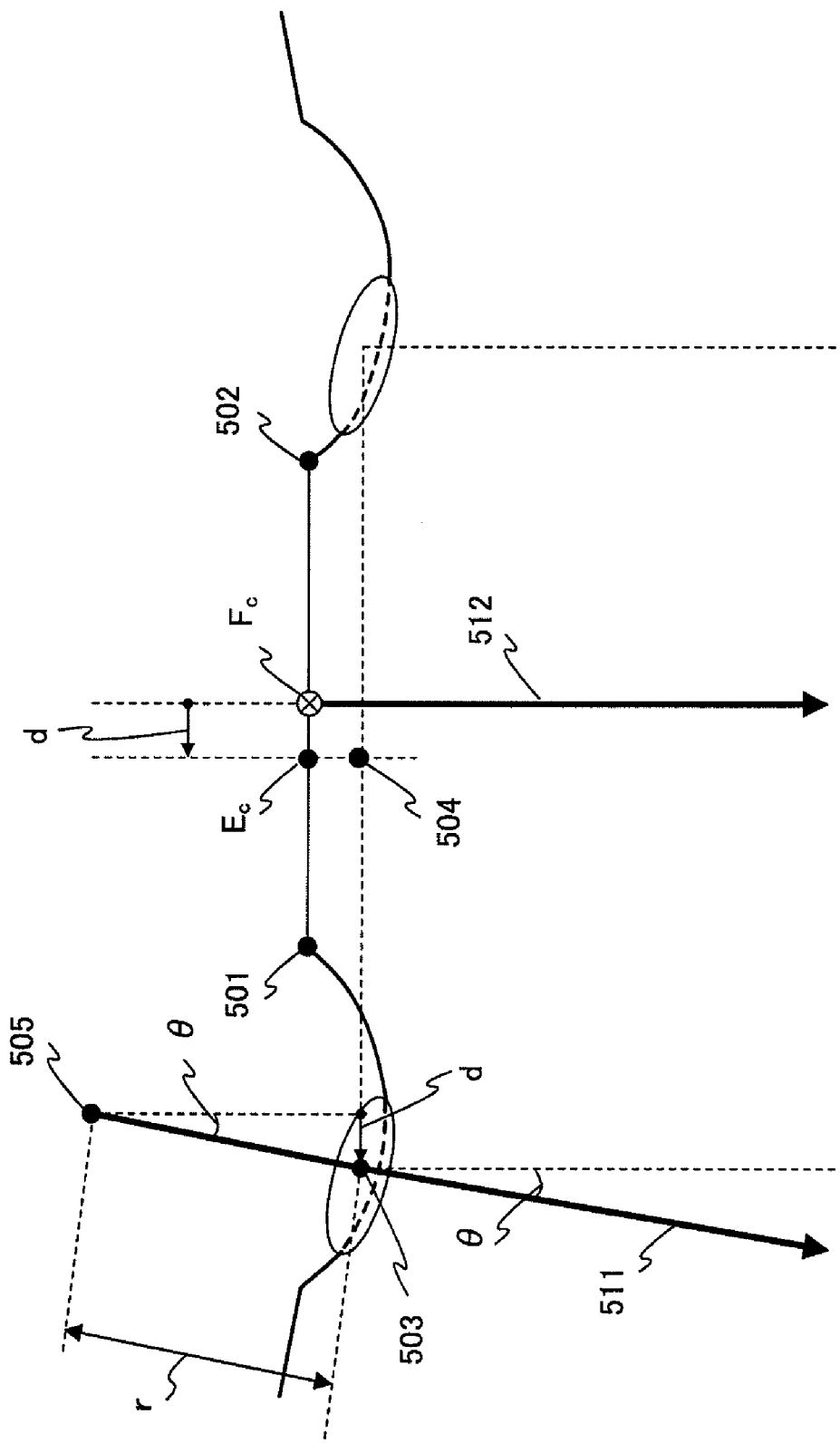
FIG. 4 illustrates relationships between parameters related to gaze direction vectors according to Embodiment 1 of the present invention.

FIG. 4 illustrates the relationships between parameters relating to a gaze direction vector, and an overhead view of the subject's eye and its surrounding region. Here, an example case will be explained where the middle point between the inner corners of the right and left eyes is the gaze direction reference point.

As shown in FIG. 4, gaze direction reference point Fc is the middle point between the inner corner of left eye 501 and the inner corner of right eye 502. Further, when pupil center 503 moves, gaze direction feature point 504 also moves, and gaze feature projection point $E_c$ moves the same distance in the lateral direction. Therefore, when pupil center 503 moves in the lateral direction for the degree of deviation d from the position of when the pupil center 503 is directed to the direction of the face front, gaze feature projection point $E_c$ also moves in the lateral direction for the degree of deviation d from gaze direction reference point Fc. Here, seeing the face from the front, the degree of deviation d originating from gaze direction reference point Fc and the angle with respect to face front vector 512 are positive in the left direction.

The degree of deviation d is the gaze direction feature measure, and, when gaze direction feature point 504 is in the left of gaze direction reference point Fc, can be calculated by, for example, following equation 1. Further, when gaze direction feature point 504 is in the right of gaze direction reference point Fc, the degree of deviation d can be calculated by, for example, following equation 2.

[1]

$$d = |\overrightarrow{E_c F_c}|$$ (Equation 1)

[2]

$$d = -|\overrightarrow{E_c F_c}|$$ (Equation 2)

In step S1900, gaze vector calculating section 173 calculates an angle formed by gaze vector 511 and face front vector 512 based on the gaze direction feature measure calculated in step S1900, and calculates gaze vector 511. Further, gaze vector calculating section 173 outputs calculated gaze vector 511 to, for example, the above-noted warning apparatus.

The rotation center of pupil center 503 originating from the face matches eyeball center 505, and therefore it is possible to represent a vector starting from eyeball center 505 and ending at pupil center 503, as gaze vector 511. Therefore, if the eyeball radius is "r," following equation 3 is established about angle θ formed by gaze vector 511 and face front 412.

(Equation 3)

$$\frac{d}{r} = \sin\theta \quad [3]$$

Therefore, angle θ formed by gaze vector 511 and face front vector 512 can be calculated by, for example, following equation 4.

(Equation 4)

$$\theta = \sin^{-1}\left(\frac{d}{r}\right) \quad [4]$$

Here, eyeball radius r varies little between adult individuals, so that it is possible to use a predetermined value. Further, depending on the characteristics of the subject such as age, gender and race, it is equally possible to change the value of eyeball radius r, and measure the actual subject's eyeball radius and use the measurement result.

Here, the coordinate system used to express the three dimensional position in three dimensional position calculating section 140, that is, the coordinate system based on photographing positions of first imaging section 111 and second imaging section 112 is referred to as a "stereo camera coordinate system." Further, a coordinate system in which a straight line passing two face parts 404 (i.e., the inner corner of left eye 501 and the inner corner of right eye 502 in FIG. 4) that are located laterally symmetrically and that derive the daze direction reference point, is the x axis and in which the z axis is parallel to face front vector 512, is referred to as a "face coordinate system."

If the components of face front vector 512 in the face coordinate system are (0, 0, $f_z$) and the components of gaze vector 511 in the face coordinate system are ($g_x$, $g_y$, $g_z$), gaze vector 511 can be calculated by, for example, following equation 5.

(Equation 5)

$$[g_x \ g_y \ g_z \ 1] = [0 \ 0 \ f_z \ 1] \cdot \begin{bmatrix} \cos\theta & 0 & -\sin\theta & 0 \\ 0 & 1 & 0 & 0 \\ \sin\theta & 0 & \cos\theta & 0 \\ 0 & 0 & 0 & 1 \end{bmatrix} \quad [5]$$

Each axis in the face coordinate system is defined based on the vector or characteristics that can be represented in the stereo camera coordinate system. Therefore, gaze vector 511 represented in the face coordinate system can be equally represented in the stereo camera coordinate system. As a result, for example, it is possible to detect in which direction in the external world the gaze vector is directed, from the external parameters of first imaging section 111 and second imaging section 112.

For example, if the components of gaze vector 511 in the stereo camera coordination system are ($G_x$, $G_y$, $G_z$) and the rotation matrix and translation vector of the face coordination system with respect to the stereo camera coordination system are R and T, respectively, gaze vector 511 in the stereo camera coordination system can be calculated by, for example, following equation 6.

[6]

$$[G_x \ G_y \ G_z] = [g_x \ g_y \ g_z] \cdot R + T \quad \text{(Equation 6)}$$

Further, it is possible to find rotation matrix R and translation vector T from the coordinates of three face parts used upon calculating face front vector 512.

In step S2000, gaze direction detecting apparatus 100 determines the end of processing for detecting gaze vector 511. This end determination is performed by, for example, receiving as input a signal commanding to stop the above warning apparatus or determining whether there is a command to stop the processing by user operation. If the processing is determined to be finished ("YES" in step S2000), a series of processing are then finished. If the processing is determined not to be finished ("NO" in step S2000), the flow returns to step S1000, and stereo image pair 400 is inputted again to detect gaze vector 511.

However, if processing is performed in parallel in a plurality of processing sections forming gaze direction detecting apparatus 100, it is possible to acquire next stereo image pair 400 before gaze vector 511 is acquired from stereo image pair 400 previously acquired. Further, image input section 110 can photograph an image at predetermined intervals. In this case, gaze direction detecting apparatus 100 determines the end in step S2000 earlier, and, upon determining the end of the processing that detects gaze vector 511, stops imaging processing in image input section 110. Here, by making shorter the time required for processing between step S1000 and step S1900, it is obviously possible to realize gaze direction detection more in real time. Further, when the processing interval for step 1000 becomes shorter, it is obviously possible to realize more accurate gaze direction detection.

Thus, gaze direction detecting apparatus 100 detects which direction the subject looks at, as gaze vector 511 and outputs the result to the warning apparatus.

In the stereo camera coordinate system, for example, the warning apparatus stores the windshield region, side mirror region and liquid crystal panel region of a car navigation apparatus, and monitors which of these regions the driver looks at based on inputted gaze vector 511. Here, for example, when the driver performs an operation of turning the steering wheel to the right or left without looking at the side mirror in the direction the driver turns the steering wheel, the warning apparatus warns the driver to check the side mirror. By this means, it is possible to prevent accidents involving people when turning the steering wheel.

As described above, according to the present embodiment, a common feature that generally applies to human faces that the centers of a person's right and left pupils are located laterally symmetrically when looking at the direction of the face front, and move in synchronization with each other when looking at different directions. To be more specific, the three dimensional positions of the centers of the right and left pupils of the eyes, and three dimensional positions of face parts that are located laterally symmetrically in the face are detected, the degree of deviation in the lateral direction from the middle point between the right and left pupil centers of the eyes and the center of the face is detected, and the gaze direction is detected based on the degree of deviation and the eyeball radius.

By this means, it is possible to acquire a gaze direction accurately, and detect the gaze direction from parameters that vary little between individuals. Therefore, it is possible to reliably acquire an accurate gaze direction detection result without having to perform calibration on a per subject basis. Further, for example, it is possible to reliably acquire an accurate gaze direction detection result from an image of low resolution by a stereo camera. That is, it is possible to reduce the resolution of a stereo camera and realize the apparatus at low cost.

Further, the direction of the face front in a specific coordinate system such as the stereo camera coordinate system is detected using face parts that are located laterally symmetrically in the person's face, so that it is possible to represent the detected gaze direction in the specific coordinate system and increase a utility value of the detection result. Further, the degree of deviation of the middle point between the right and left pupils of the eyes in the lateral direction with respect to the center of the face is detected based on images photographed by a stereo camera, so that it is possible to realize non-contact gaze direction detection and apply this technique to various fields flexibly. Further, by utilizing the above-noted feature that applies common to human faces and by furthermore defining a known value as the radius of the eyeball, which varies little between individuals, it is completely unnecessary to perform calibration on a per subject basis. By this means, it is possible to start gaze direction detection in shorter time and reduce the burden for the user. That is, it is possible to detect the direction of the person's gaze in an easier and simpler manner.

In particular, when the present invention is applied to a warning apparatus that warns the driver of the risks of accidents, non-contact gaze direction detection needs to be performed using a stereo camera. However, the brightness or illuminated condition in the car during driving fluctuates greatly, and, consequently, uncertain elements such as shade are likely to be included in the image. Therefore, the gaze direction detecting apparatus according to the present embodiment is especially useful for such a warning apparatus.

Further, although the gaze direction detecting apparatus according to the present embodiment performs gaze direction detection only depending on the movement of the pupil in the lateral direction with respect to the face, generally, the human pupil moves more in the lateral direction than in vertical directions, so that the gaze direction detecting apparatus can reliably acquire a detection result of high use value as information to specify what a person pays attention to or thinks. Further, it is obviously possible to combine the gaze direction detecting apparatus with a technique of gaze direction detection depending on the movement of the pupils in the vertical direction with respect to the face.

(Embodiment 2)

In above-described Embodiment 1, although the gaze feature projection point is used to calculate the degree of deviation of the middle point between the centers of the right and left pupils in the lateral direction, the reference plane that is located in the center of the face in the lateral direction is calculated, and this calculated reference plane (i.e., symmetric plane) is used in the present embodiment.

Figure 5:
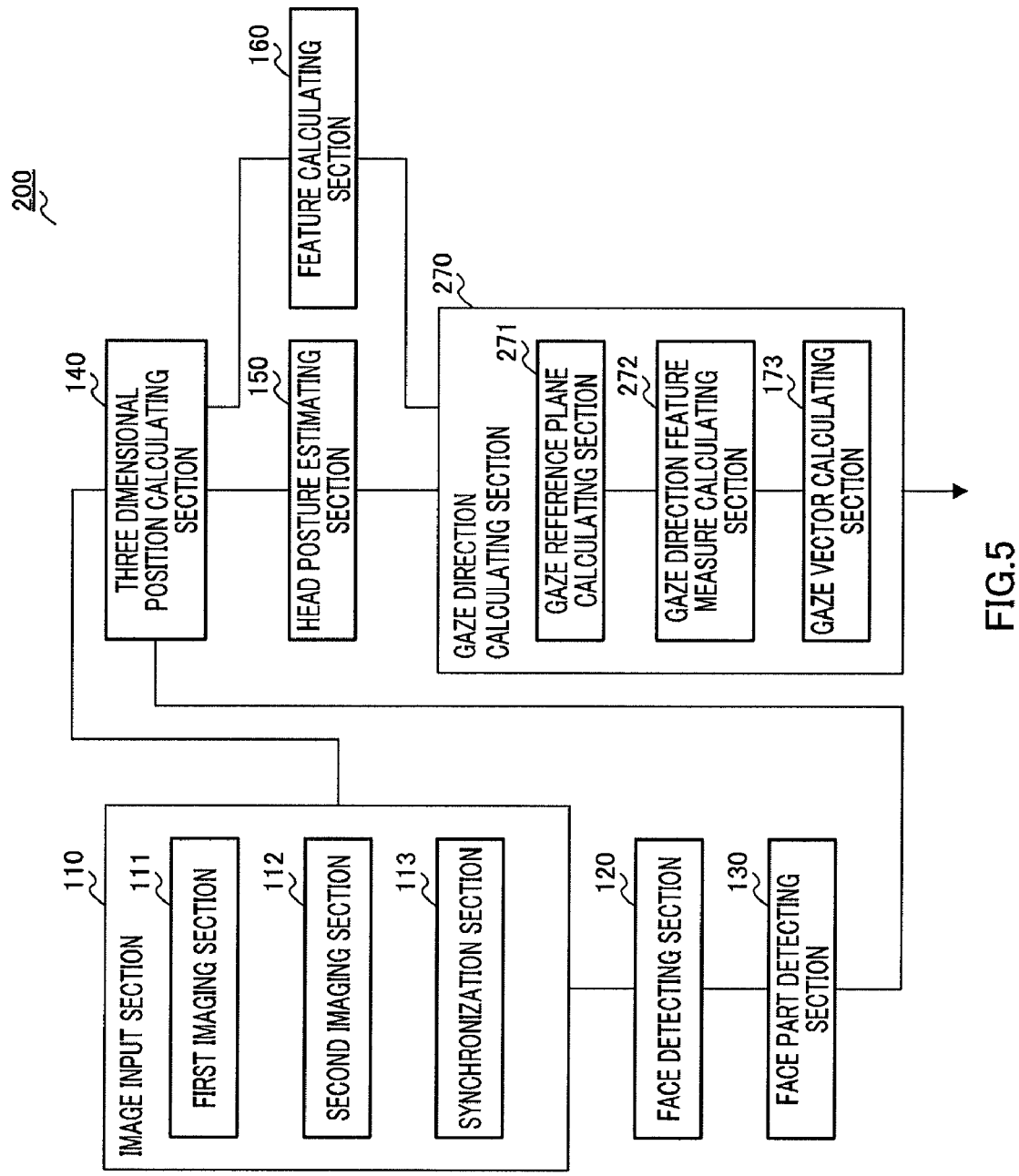
FIG. 5 is a block diagram showing the configuration of a gaze direction detecting apparatus according to Embodiment 2 of the present invention.

FIG. 5 is a block diagram showing the configuration of the gaze direction detecting apparatus according to Embodiment 2 of the present invention, and is associated with FIG. 1 of Embodiment 1.

In FIG. 5, gaze direction detecting apparatus 200 of the present embodiment provides gaze direction calculating section 270 instead of gaze direction calculating section 170 shown in FIG. 1. Gaze direction calculating section 270 provides gaze reference plane calculating section 271 and gaze direction feature measure calculating section 272 instead of gaze feature measure projection section 171 and gaze direction feature measure calculating section 172.

In gaze direction calculating section 270, gaze reference plane calculating section 271 calculates the three dimensional position (i.e., reference position) of the gaze reference plane equivalent to the symmetric plane of the face. Gaze direction feature measure calculating section 272 calculates the degree of deviation of the gaze direction feature point with respect to the gaze reference plane as the gaze direction feature measure.

Figure 6:
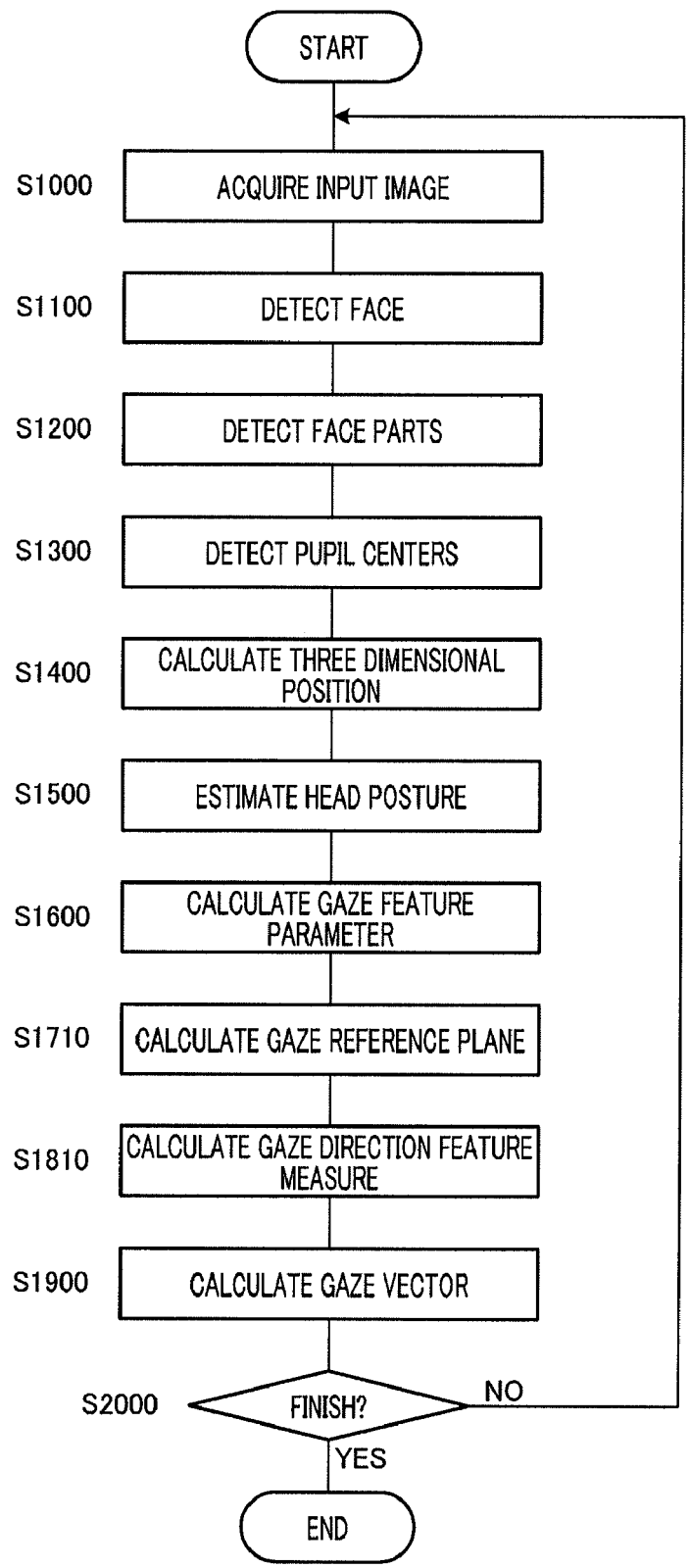
FIG. 6 is a flowchart showing the flow of gaze direction detection processing in a gaze direction detecting apparatus according to Embodiment 2 of the present invention.

FIG. 6 is a flowchart showing the flow of gaze direction detection processing in gaze direction detecting apparatus 200, and is associated with FIG. 2 of Embodiment 1.

The processing in steps S1000 to S1600 are the same as in FIG. 2. In step S1600, when feature calculating section 160 acquires a gaze feature parameter, the flow proceeds to step S1710.

In step S1710, gaze reference plane calculating section 271 calculates the above gaze reference plane based on the face part three dimensional position information acquired in step S1400 and the gaze feature parameter acquired in step S1600. Here, the gaze reference plane is defined as a plane passing the gaze direction reference point and having as a normal a straight line passing two face parts 404 that are located laterally symmetrically and that derive the gaze direction reference point.

First, gaze reference plane calculating section 271 calculates a vector connecting two face parts 404 (hereinafter "face part vector") that are located laterally symmetrically and that derive gaze direction reference point Fc. Further, gaze reference plane calculating section 271 calculates the gaze reference plane based on the calculated face part vector and gaze direction reference point.

Figure 7:
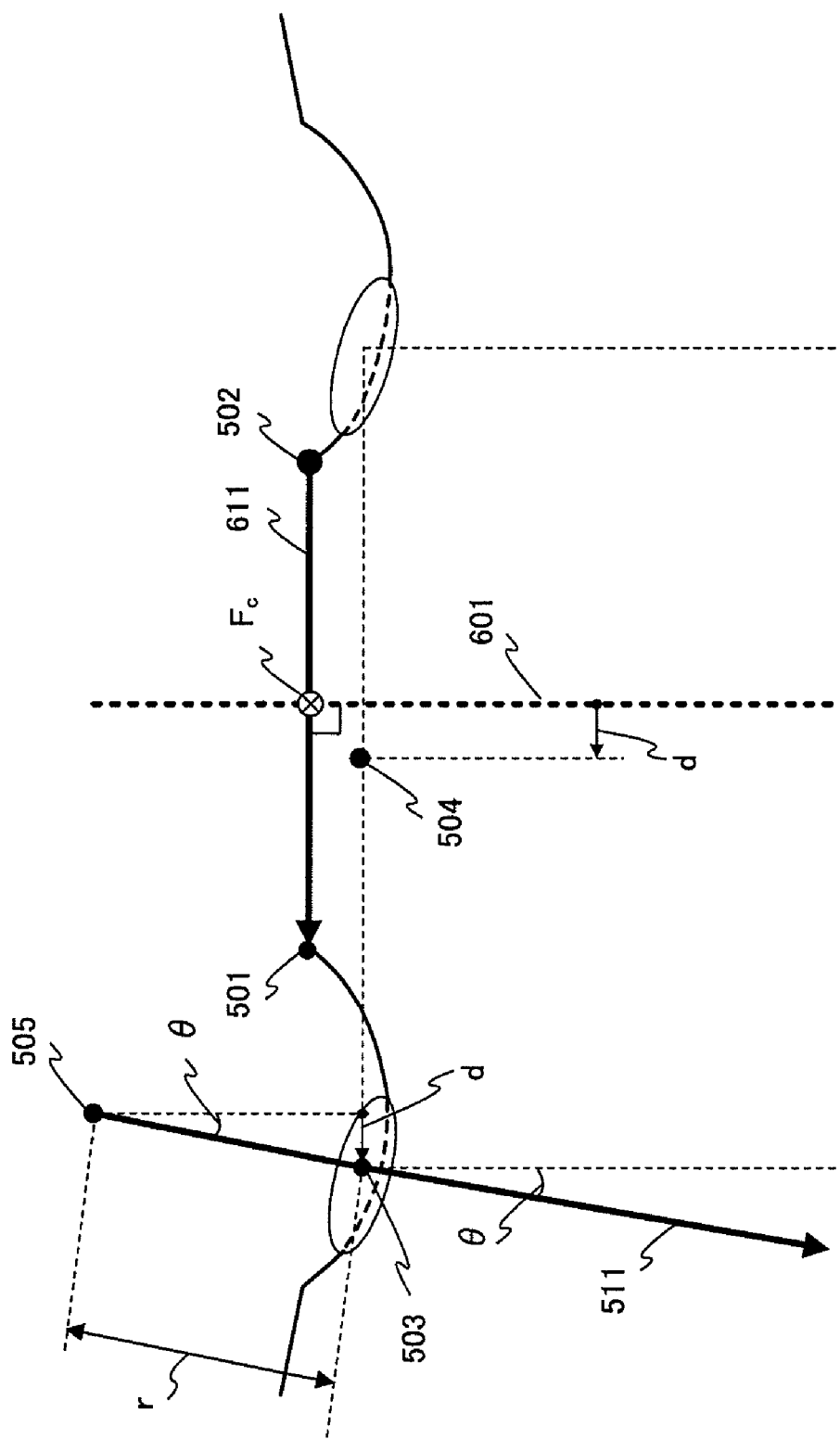
FIG. 7 illustrates the relationships between parameters related to gaze direction vectors according to Embodiment 2 of the present invention.

FIG. 7 illustrates the relationships between parameters related to a gaze direction vector, and is associated with FIG. 4 of Embodiment 1.

As shown in FIG. 7, gaze reference plane 601 is orthogonal to a straight line passing two face parts 404 (the inner corner of the left eye 501 and the inner corner of the right eye 502 in FIG. 7) that are located laterally symmetrically and that derive gaze direction reference point Fc, and passes gaze direction reference point Fc. When the components of face part vector 611 are (a, b, c) and the coordinates of Fc are ($x_f$, $y_f$, $z_f$), gaze reference plane 601 can be expressed by, for example, following equation 7.

[7]

$$a(x-x_f)+b(y-y_f)+c(z-z_f)=0 \quad \text{(Equation 7)}$$

In step S1810, based on gaze direction feature point 504 acquired in step S1600 and gaze reference plane 601 acquired in step S1710, gaze direction feature measure calculating section 272 calculates the degree of deviation d of gaze direction feature point 504 with respect to gaze reference plane 601.

When the coordinates of gaze direction feature point 504 are ($x_p$, $y_p$, $z_p$), if gaze direction feature point 504 is in the left of gaze reference plane 601, it is possible to calculate the degree of deviation d, namely, the gaze direction feature measure using, for example, following equation 8. Further, if gaze direction feature point 504 is in the right of gaze reference plane 601, it is possible to calculate the degree of deviation d using, for example, following equation 9.

(Equation 8)

$$d = \frac{|a(x_p - x_f) + b(y_p - y_f) + c(z_p - z_f)|}{\sqrt{a^2 + b^2 + c^2}} \quad [8]$$

(Equation 9)

$$d = -\frac{|a(x_p - x_f) + b(y_p - y_f) + c(z_p - z_f)|}{\sqrt{a^2 + b^2 + c^2}} \quad [9]$$

In FIG. 6, when the gaze direction feature measure is calculated in step S1810 as described above, the flow proceeds to step S1900. The processing in step S1900 or later is the same as in FIG. 2, and gaze vector 511 is calculated in step S1900. For this calculation, for example, it is possible to use equations 3, 4, 5 and 6 in Embodiment 1 using a known value as eyeball radius r.

As described above, according to the present embodiment, as in Embodiment 1, it is possible to reliably acquire an accurate gaze direction detection result without having to perform calibration on a per subject basis. Further, although the accuracy of the gaze direction feature measure in Embodiment 1 fluctuates according to selection of face parts deriving the distance between the gaze direction projection point and the gaze feature point, that is, according to selection of face parts deriving the face direction reference point, the gaze reference plane is made the reference in the present embodiment, so that it is possible to reduce random accuracy. Therefore, compared to Embodiment 1, it is possible to improve the accuracy of detecting gaze vectors.

(Embodiment 3)

For example, when gaze direction detection is performed for a person driving a car, the direction of the face changes in a wide range, and, consequently, only one eye may be photographed temporarily. With the present embodiment, information about photographed both eyes is stored to continuously detect the gaze direction even when only one eye can be temporarily photographed.

Figure 8:
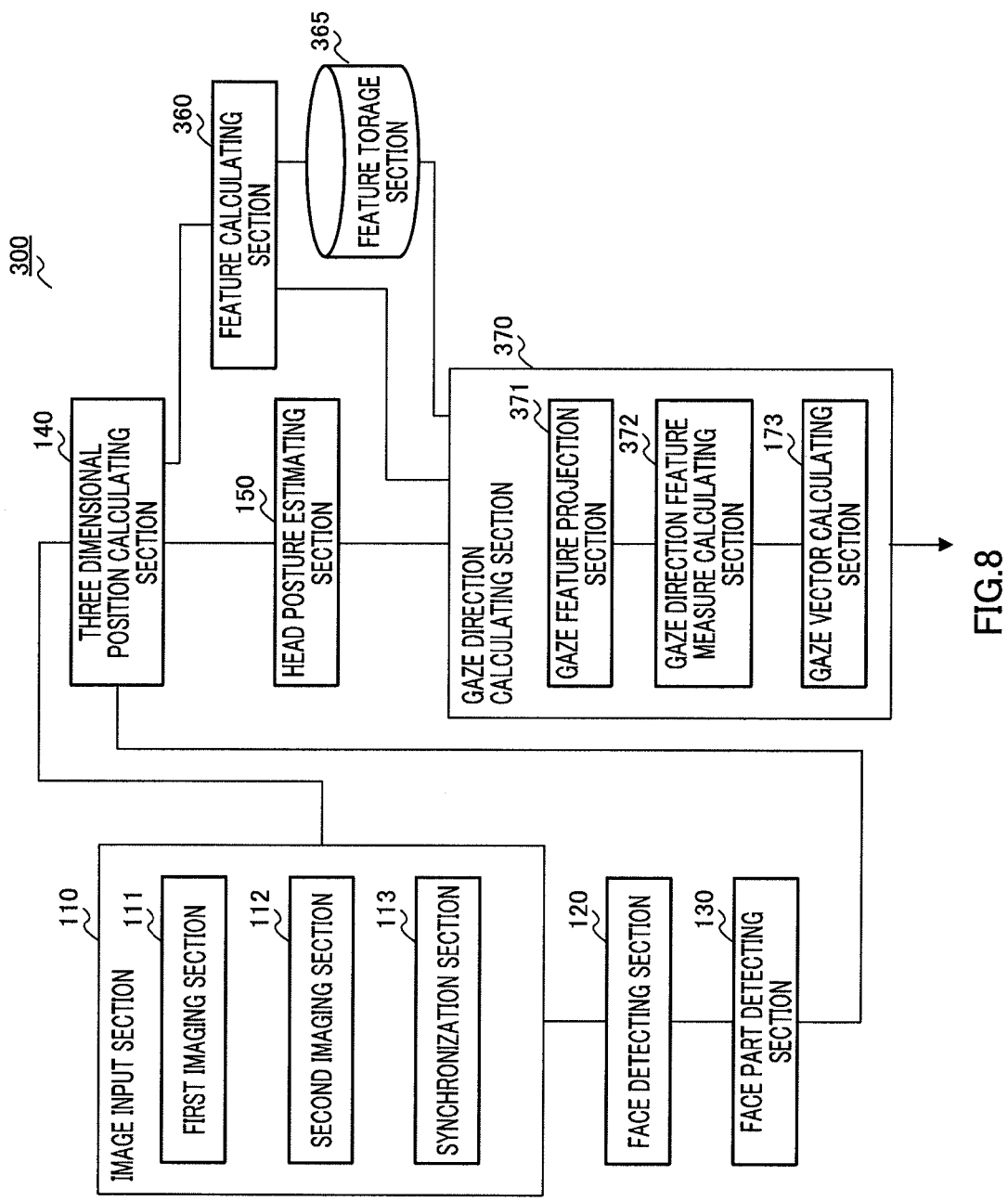
FIG. 8 is a block diagram showing the configuration of a gaze direction detecting apparatus according to Embodiment 3 of the present invention.

FIG. 8 is a block diagram showing the configuration of the gaze direction detecting apparatus according to Embodiment 3 of the present invention, and is associated with FIG. 1 of Embodiment 1.

In FIG. 8, gaze direction detecting apparatus 300 of the present embodiment provides feature calculating section 360 and gaze direction calculating section 370 instead of feature calculating section 160 and gaze direction calculating section 170 shown in FIG. 1. Gaze direction calculating section 370 provides gaze feature projection section 371 and gaze direction feature measure calculating section 372 instead of gaze feature projection section 171 and gaze direction feature measure calculating section 172 shown in FIG. 1. Further, gaze direction detecting apparatus 300 provides feature storage section 365.

Feature calculating section 360 acquires a gaze feature parameter and the inter-pupil distance, which is the distance between the centers of the right and left pupils, from the face part three dimensional position information inputted from three dimensional position calculating section 140. However, with the present embodiment, the gaze feature parameter only needs to include the gaze direction reference point, and needs not include the gaze direction feature point every time.

Feature storage section 365 stores the inter-pupil distance calculated in feature calculating section 360.

In gaze direction calculating section 370, gaze feature projection section 371 calculates a projection point (hereinafter "face part projection point") at which the center of the adequate one of the centers of the right and left pupils is projected on a straight line passing face parts 404 deriving the gaze direction reference point. Gaze direction feature measure calculating section 372 calculates the gaze direction feature measure based on the face part projection point, gaze feature parameter and inter-pupil distance stored in feature storage section 365.

Figure 9:
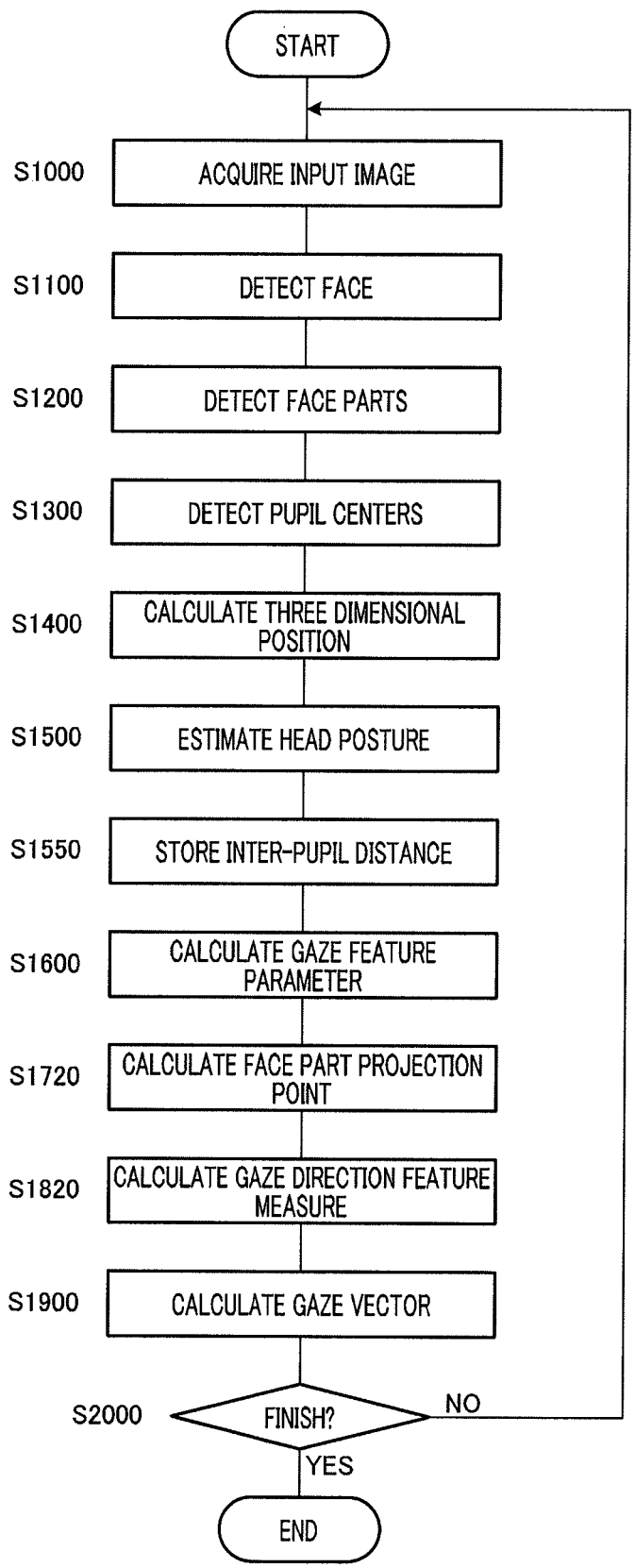
FIG. 9 is a flowchart showing the flow of gaze direction detection processing in a gaze direction detecting apparatus according to Embodiment 3 of the present invention.

FIG. 9 is a flowchart showing the flow of gaze direction detection processing in gaze direction detecting apparatus 300, and is associated with FIG. 2 of Embodiment 1.

The processing in step S1000 to S1500 are the same as in FIG. 2. In step S1500, when head posture estimating section 150 acquires a head posture parameter, the flow proceeds to step S1550.

In step S1550, feature calculating section 360 acquires a gaze feature parameter (i.e., gaze direction reference point), calculates the inter-pupil distance based on the three dimensional positions of the centers of the right and left pupils of the subject, and makes feature storage section 365 store the calculated inter-pupil distance. If feature storage section 365 already stores past information, the storage content is updated when the new inter-pupil distance is calculated.

However, if first imaging section 111 and second imaging section 112 cannot photograph images of the centers of the right and left pupils since, for example, the face is directed to the side or the reflection of the lens of glasses is high, the flow directly proceeds to step S1600 without acquiring a gaze direction feature point and calculating and storing the inter-pupil distance. Further, if feature storage section 365 already stores the inter-pupil distance of the same subject acquired in the past, the flow may directly proceeds to step S1600 without calculating and storing the inter-pupil distance.

In step S1600, feature calculating section 360 calculates a gaze feature parameter based on the three dimensional positions of pupil center 405 and face parts 404 detected in step S1400, and the flow proceeds to step S1720.

In step S1720, based on the face part three dimensional position information acquired in step S1400 and the gaze feature parameter acquired in step S1600, gaze feature projection section 371 projects one of the centers of the right and left pupils to a straight line passing two face parts 404 that are located laterally symmetrically and that derive the gaze direction reference point, and acquires the projection point as the face part projection point.

In step S1820, gaze direction feature measure calculating section 372 calculates the gaze direction feature measure based on the gaze direction reference point acquired in step S1550 and the face part projection point acquired in step S1720.

Figure 10:
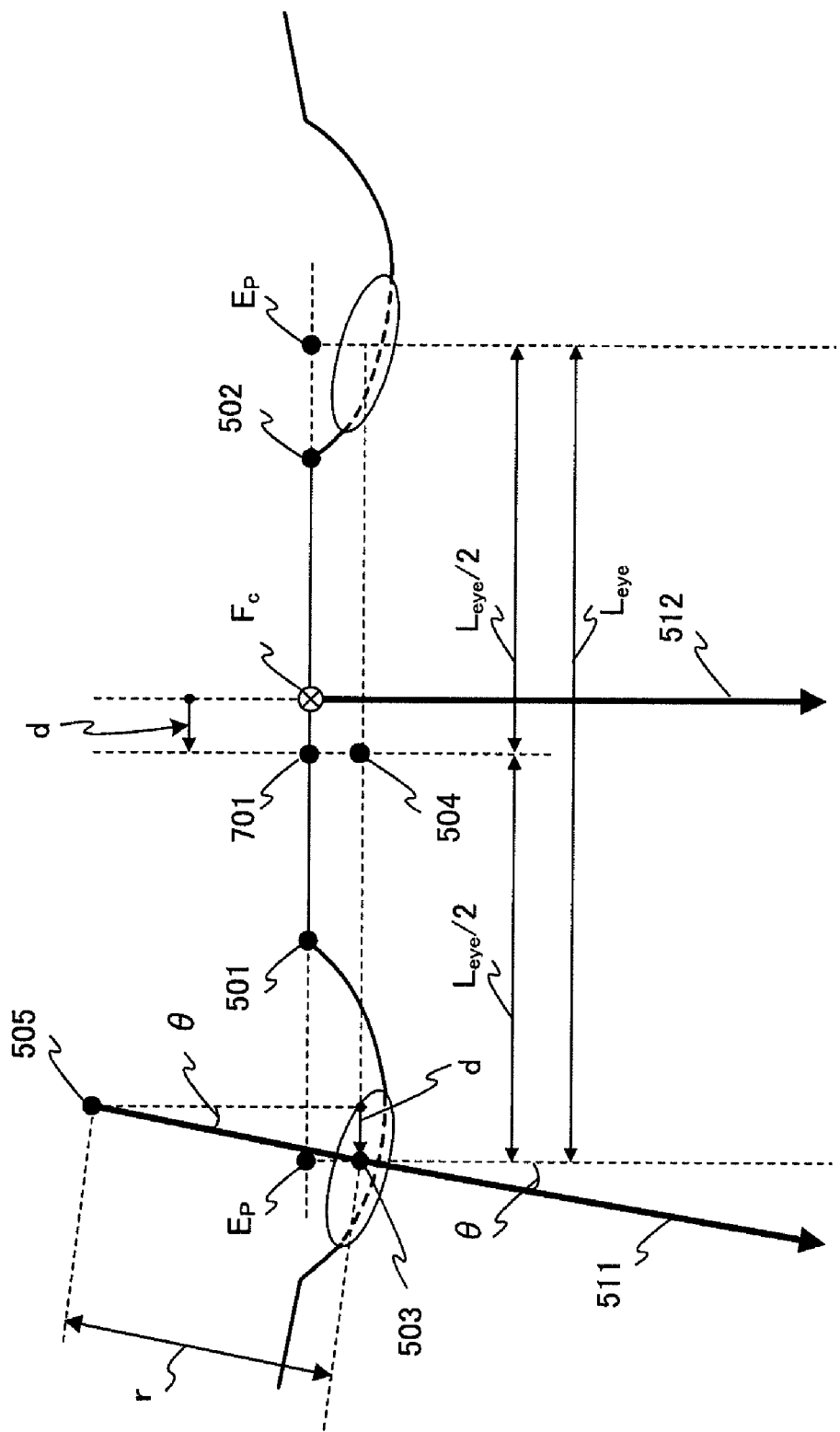
FIG. 10 illustrates the relationships between parameters related to gaze direction vectors according to Embodiment 3 of the present invention.

FIG. 10 illustrates the relationships between parameters related to the gaze direction vector, and is associated with FIG. 4 of Embodiment 1.

As shown in FIG. 10, when pupil center 503 moves, the three dimensional position (i.e., feature position) of middle point 701 between right and left face part projection points $E_p$, which are projected on the straight line passing two face parts 404 (i.e., the inner corner of left eye 501 and the inner corner of right eye 502 in FIG. 10) deriving gaze direction reference point Fc, also moves for the same degree of deviation in the lateral direction. Therefore, if the position of pupil center 503 moves in the right and left directions for the degree of deviation d when pupil center 503 is directed to the direction of the face front, middle point 701 between the right and left face part projection points $E_p$ also moves for the degree of deviation d in the right and left directions with respect to gaze direction reference point Fc.

The degree of deviation d is the gaze direction feature measure, and, if the inter-pupil distance is $L_{eye}$ and middle point 701 between the right and left face part projection points $E_p$ is in the left of gaze direction reference point Fc, can be calculated by, for example, following equation 10. Further, if middle point 701 between the right and left face part projection points $E_p$ is in the right of gaze direction reference point Fc, the degree of deviation d can be calculated by, for example, following equation 11.

[10]

$$d = \|\overline{E_p F_c}\| - 0.5 L_{eye}\| \quad \text{(Equation 10)}$$

[11]

$$d = -\|\overline{E_p F_c}\| - 0.5 L_{eye}\| \quad \text{(Equation 11)}$$

The value calculated from above-noted equations 10 and 11 is the same regardless of whether right face part projection point $E_p$ is used or left face part projection point $E_p$. Therefore, upon calculating the gaze direction feature measure, it is possible to use an arbitrary one of right and left face part projection points $E_p$. In other words, if gaze direction reference point Fc and inter-pupil distance $L_{eye}$ are acquired, it is possible to calculate a gaze direction feature measure from the three dimensional position of one of right and left pupil centers 503. That is, the right and left pupil centers need not be photographed every time, and, for example, even when only one eye can be temporarily photographed since the face is directed to the side, it is possible to continuously calculate the gaze direction feature measure.

In FIG. 10, when the gaze direction feature measure is calculated in step S1820 as described above, the flow proceeds to step S1900. The processing in step S1900 or later is the same as in FIG. 2, and, in step S1900, gaze vector 511 is calculated. In this calculation, for example, it is possible to use equations 3, 4, 5 and 6 in Embodiment 1 using a known value for eyeball radius r.

As described above, according to the present embodiment, as in Embodiments 1 and 2, it is possible to reliably acquire an accurate gaze direction detection result without having to perform calibration on a per subject basis. Further, the middle point between the right and left face part projection points can be specified from the center of one pupil, so that, even when only one eye can be photographed, it is always possible to find the degree of deviation of the center of the pupil with respect to the face front in the lateral direction.

That is, according to the present embodiment, even when only one eye of the subject can be photographed due to the face direction, hair, rims of glasses, reflection of light or other reasons, it is possible to detect the gaze direction and acquire an accurate gaze direction detection result more reliably. It is possible to select as the detection target of three dimensional position, the center of the pupil of the opposite side to the side of the face viewed from first imaging section 111 and second imaging section 112, such that the right eye is selected when the face is directed to the left and the left eye is selected when the face is directed to the right.

Further, for example, by separately detecting the inter-pupil distance and inputting the inter-pupil distance as an initial value, it is possible to store the inter-pupil distance in advance. Further, when the centers of the right and left pupils are detected, by calculating the gaze direction feature measure by the method explained in Embodiment 1 or Embodiment 2, it is possible to apply the method explained in the present embodiment only when the center of only one pupil can be detected. In this case, whether the centers of the right and left pupils are detected needs to be determined to change processing according to the determination result.

(Embodiment 4)

A case will be explained with Embodiment 4 where the gaze direction detection using the three dimensional position of the center of one pupil explained in Embodiment 3 is performed using the gaze reference plane explained in Embodiment 2.

Figure 11:
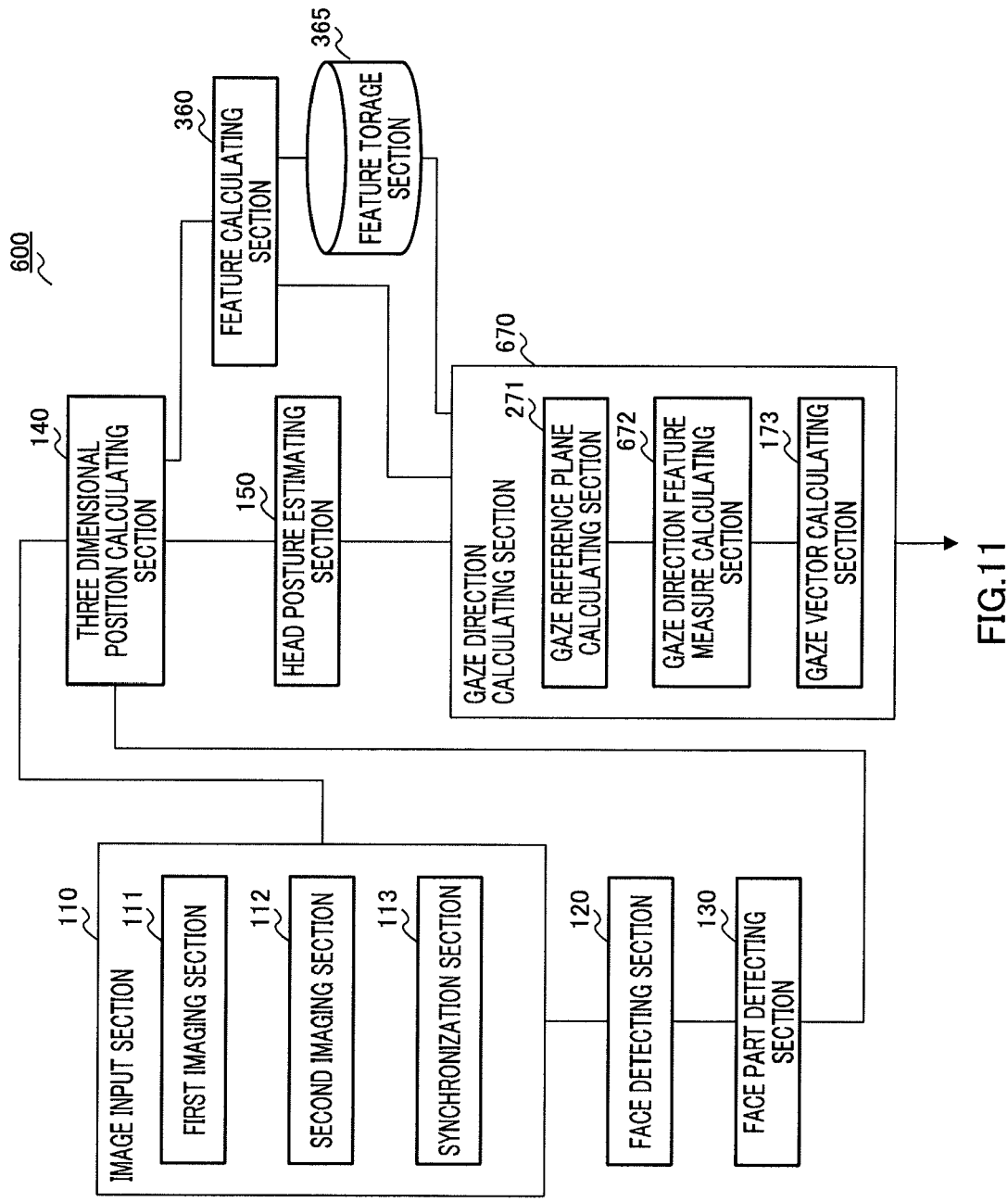
FIG. 11 is a block diagram showing the configuration of a gaze direction detecting apparatus according to Embodiment 4 of the present invention.

FIG. 11 is a block diagram showing the configuration of the gaze direction detecting apparatus according to Embodiment 4 of the present invention, and is associated with FIG. 5 of Embodiment 2 and FIG. 8 of Embodiment 3.

In FIG. 11, gaze direction detecting apparatus 600 of the present embodiment provides gaze direction calculating section 670 instead of gaze direction calculating section 370 shown in FIG. 8. Gaze direction calculating section 670 provides gaze direction reference plane calculating section 271 shown in FIG. 5 and gaze direction feature measure calculating section 672 instead of gaze direction feature projection section 371 and gaze direction feature measure calculating section 372 shown in FIG. 8.

In gaze direction calculating section 670, gaze direction feature measure calculating section 672 calculates the gaze direction feature measure based on the three dimensional position of the gaze reference plane calculated in gaze reference plane calculating section 271, the gaze feature parameter calculated in feature calculating section 360 and the inter-pupil distance stored in feature storage section 365.

Figure 12:
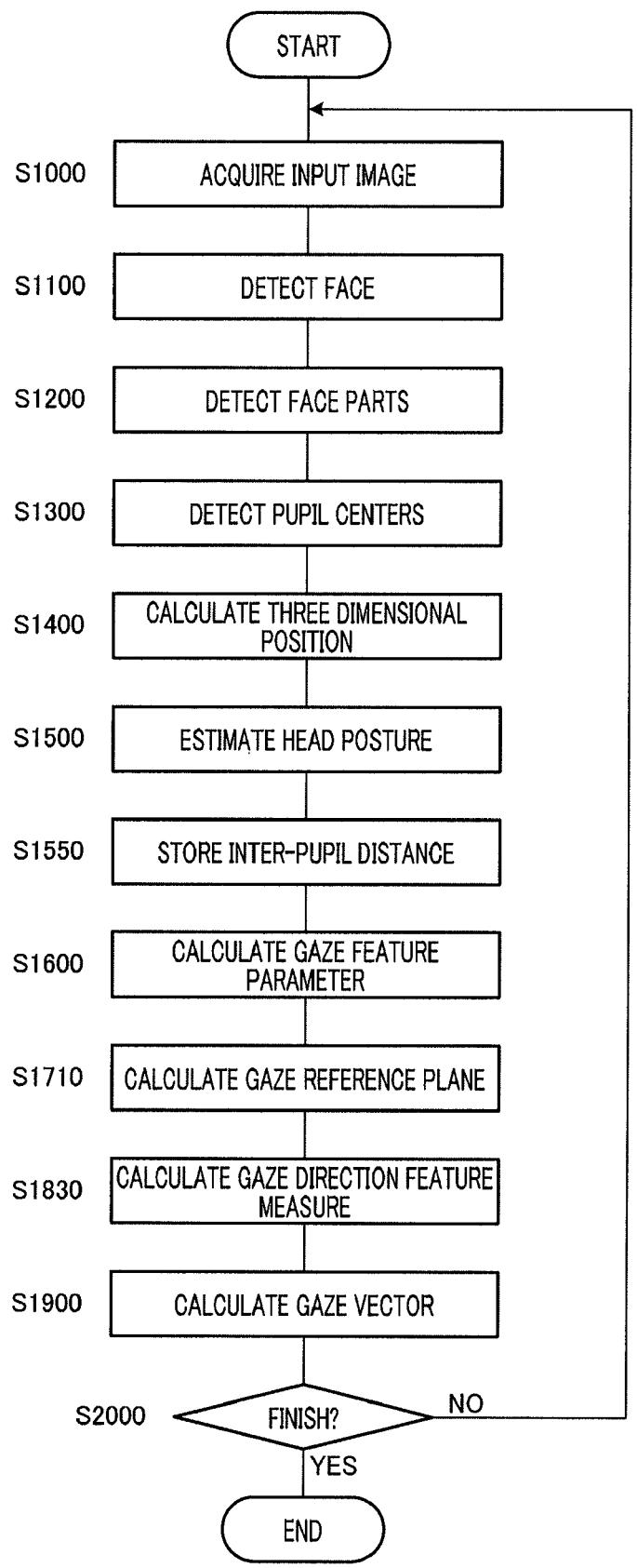
FIG. 12 is a flowchart showing the flow of gaze direction detection processing in a gaze direction detecting apparatus according to Embodiment 4 of the preset invention.

FIG. 12 is a flowchart showing the flow of gaze direction detection processing in gaze direction detecting apparatus 600, and is associated with FIG. 6 of Embodiment 2 and FIG. 9 of Embodiment 3.

The processing in steps S1000 to S1600 are the same as in FIG. 9. Further, the processing in step S1710 and the processing in step S1900 and later are the same as in FIG. 6 except that the processing in step S1810 is replaced by the processing in step S1830.

In step S1830, gaze direction feature measure calculating section 672 calculates the gaze direction feature measure based on the three dimensional position of the center of the pupil detected in step S1400, the inter-pupil distance calculated in step S1550 and the gaze reference plane calculated in step S1710.

Figure 13:
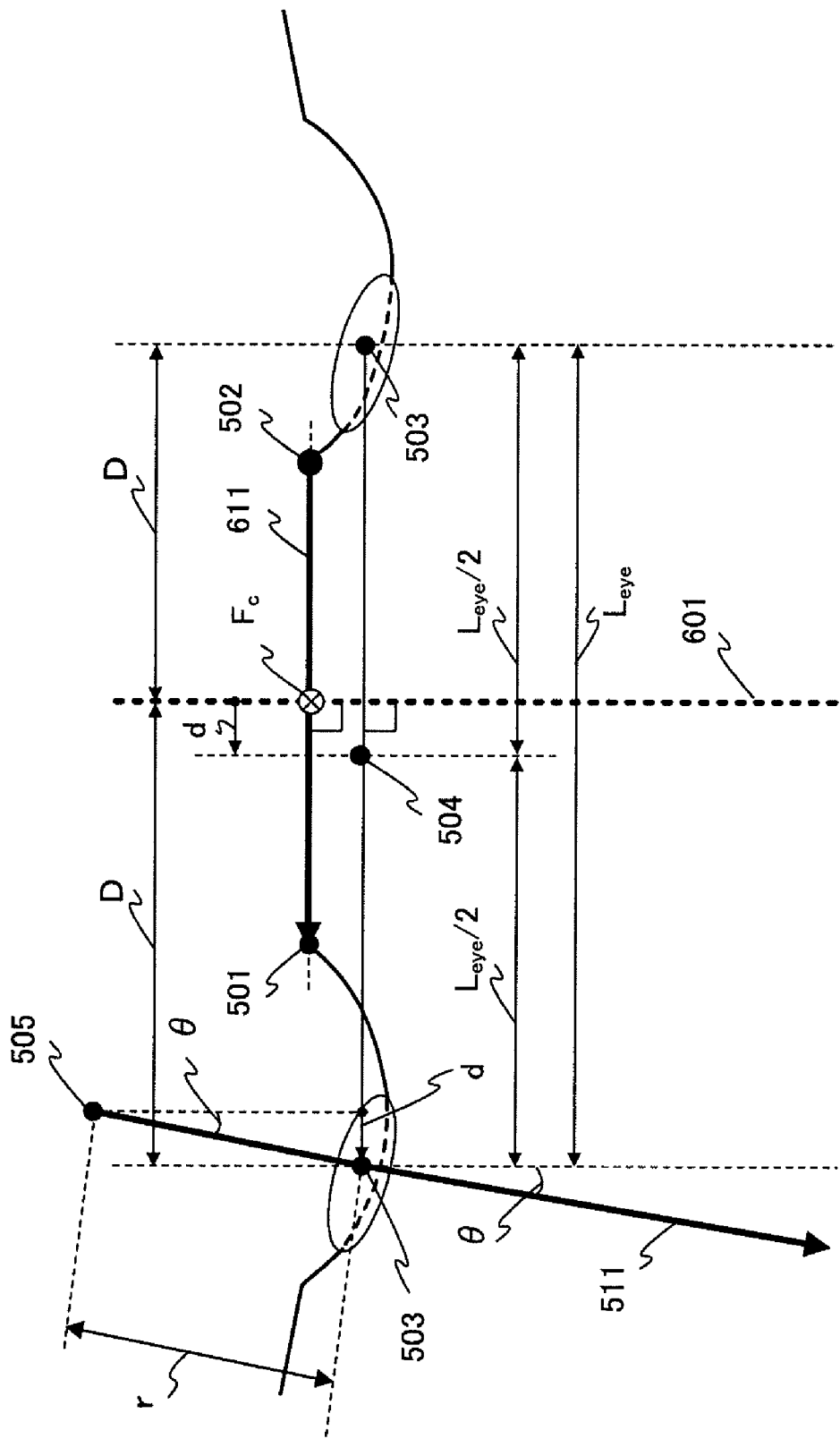
FIG. 13 illustrates the relationships between parameters related to gaze direction vectors according to Embodiment 4 of the present invention.

FIG. 13 illustrates the relationships between parameters related to the gaze direction vector, and is associated with FIG. 7 of Embodiment 2 and FIG. 10 in Embodiment 3.

As shown in FIG. 13, when pupil center 503 moves in the lateral direction for the degree of deviation d from the position of when the pupil center 503 is directed to the direction of the face front, gaze direction feature point 504, which is the middle point between right and left pupil centers 503, also moves for degree of deviation d in the right and left directions based on gaze direction reference plane 601. Further, the straight line connecting right and left pupil centers 503 is orthogonal to gaze reference plane 601. Therefore, the difference between a half of inter-pupil distance $L_{eye}$ and distance D between gaze reference plane 601 and one of right and left pupil centers 503, is the degree of deviation d.

If the components of face part vector 611 are (a, b, c), the coordinates of gaze direction reference point Fc are $(x_f, y_f, z_f)$, and the coordinates of the center of one of the right and left pupils are $(x_q, y_q, z_q)$, distance D between gaze reference plane 601 and pupil center 503 can be calculated by, for example, following equation 12.

(Equation 12)

$$D = \frac{|a(x_q - x_f) + b(y_q - y_f) + c(z_q - z_f)|}{\sqrt{a^2 + b^2 + c^2}} \quad [12]$$

Therefore, if pupil center 503 used for the calculation is in the left of gaze direction reference point $F_c$, the degree of deviation d that serves as the gaze direction feature measure can be calculated by, for example, following equation 13. Further, if pupil center 503 used for calculation is in the right side of gaze direction reference point Fc, the degree of deviation d can be calculated by, for example, following equation 14.

(Equation 13)

$$d = D - 0.5 L_{eye} \quad [13]$$
$$= \frac{|a(x_q - x_f) + b(y_q - y_f) + c(z_q - z_f)|}{\sqrt{a^2 + b^2 + c^2}} - 0.5 L_{eye}$$

(Equation 14)

$$d = -(D - 0.5 L_{eye}) \quad [14]$$
$$= -\left(\frac{|a(x_q - x_f) + b(y_q - y_f) + c(z_q - z_f)|}{\sqrt{a^2 + b^2 + c^2}} - 0.5 L_{eye}\right)$$

The value calculated from above-noted equations 13 and 14 is the same, regardless of whether right pupil center 503 is used or left pupil center 503 is used. Therefore, as in Embodiment 3, upon calculating the gaze direction feature measure, it is possible to use an arbitrary one of right and left pupil centers 503.

As described above, according to the present embodiment, as in Embodiment 3, even when only one eye can be photographed, it is possible to detect the gaze direction and acquire an accurate gaze direction detection result more reliably. Further, the three dimensional position of the center of the pupil can be directly used with reference to the gaze reference plane, so that it is possible to improve the accuracy of gaze direction detection compared to Embodiment 3.

(Embodiment 5)

A case will be explained with Embodiment 5 where, when the three dimensional positions of the centers of the pupils of the right and left eyes can be acquired, gaze direction detection is performed using the eye of the higher reliability of the acquired three dimensional position.

When the face is directed to the right or left, the depth of the eye on the rear side from the image sensor (hereinafter "camera") of first imaging section 111 and second imaging section 112 that function as stereo cameras, is deep from the camera, and therefore is photographed in a relatively small size. Further, when a light transmitter is placed near the camera as the light source for photographs, the eye on the rear side in the opposite side to the side of the face seen from the camera is not likely to be exposed to light, and, consequently, the eye is often black out in the image. Therefore, when the face is directed to the right or left greatly with respect to the optical axis, the accuracy of the image of the eye on the rear side seen from the camera may degrade significantly.

When the accuracy of the image degrades, the accuracy of detecting the three dimensional position of the center of the pupil also degrades. For this reason, by performing gaze direction detection using only the three dimensional position of the center of the pupil of the eye on the front side even when both eyes can be photographed, it is possible to secure reliable detection accuracy. Therefore, with the present embodiment, which one of the right and left eyes is the eye on the front side is determined according to which direction the face is directed toward, to perform gaze direction detection using gaze reference plane and information acquired from the eye on the front side from which information of higher reliability can be acquired.

Figure 14:
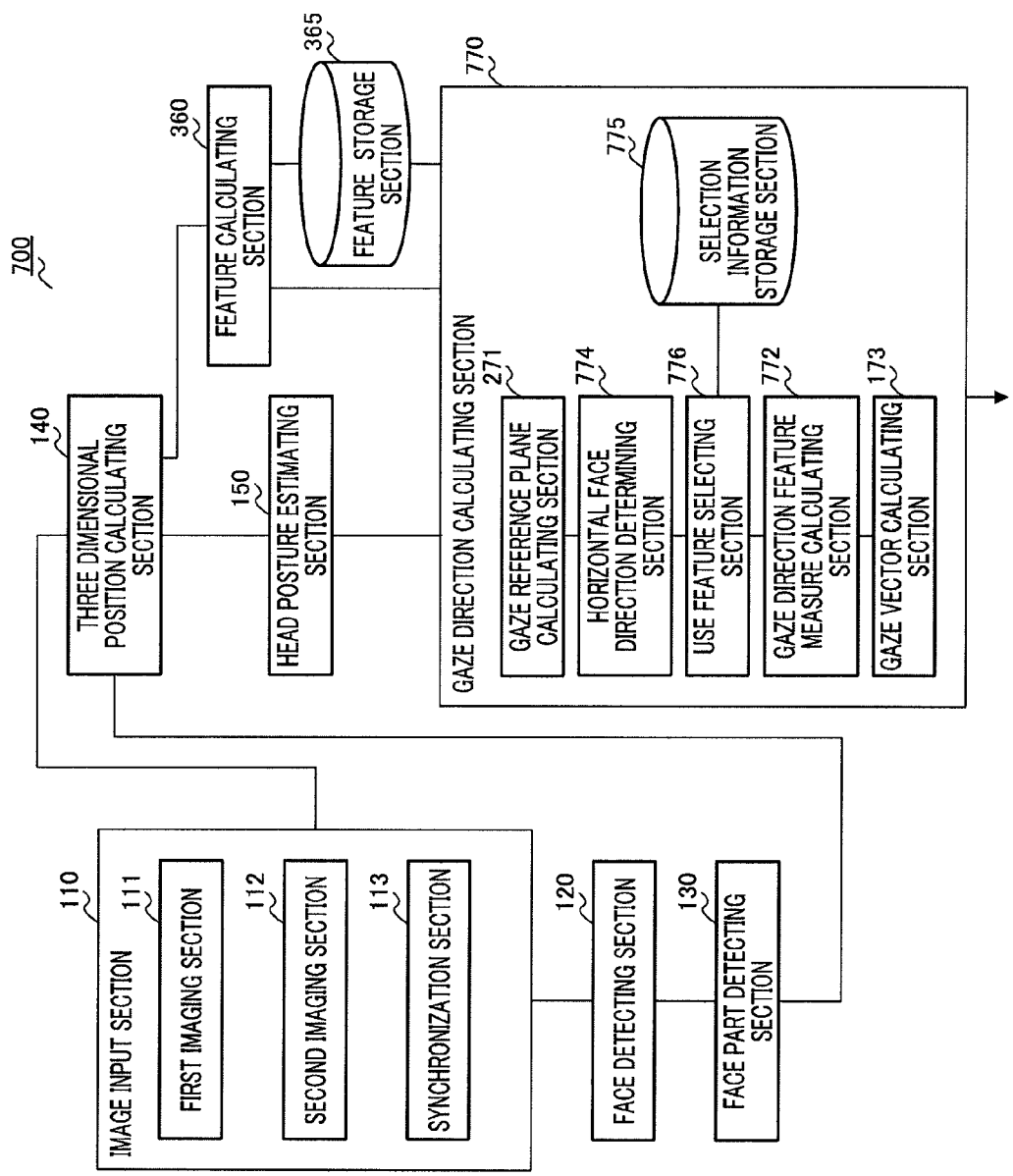
FIG. 14 is a block diagram showing the configuration of a gaze direction detecting apparatus according to Embodiment 5 of the present invention.

FIG. 14 is a block diagram showing the configuration of the gaze direction detecting apparatus according to Embodiment 5 of the present invention, and is associated with FIG. 11 in Embodiment 4.

In FIG. 14, gaze direction detecting apparatus 700 of the present embodiment provides gaze direction calculating section 770 instead of gaze direction calculating section 670 shown in FIG. 11. Gaze direction calculating section 770 provides horizontal face direction determining section 774, selection information storage section 775, use feature selecting section 776 and gaze direction feature measure calculating section 772 instead of gaze direction feature measure calculating section 672 shown in FIG. 11.

In gaze direction calculating section 770, horizontal face direction determining section 774 determines which lateral direction the face is directed to in the stereo camera coordinate system based on the face front vector acquired in head posture estimating section 150, and generates face direction information indicating whether the face is directed to the right or left seen from the camera.

Selection information storage section 775 stores a selection information table describing in advance which eye should be selected according to the direction of the face.

FIG. 15 illustrates an example of content of a selection information table.

As shown in FIG. 15, selection information table 775a describes which direction the face is directed to seen from the camera and which eye should be used in the calculation of gaze direction detection. The face direction "left" is associated with "right eye" as the eye to be used. The face direction "right direction" is associated with "left eye" as the eye to be used. That is, selection information table 775a describes the eye on the front side, namely, the eye from which the gaze direction can be detected at more secure accuracy, in association with the face direction.

With reference to selection information table 775a, use feature selecting section 776 in FIG. 14 selects the eye to be used, according to the face direction indicated from the face direction information generated in horizontal face direction determining section 774. Further, use feature selecting section 776 generates pupil selection information indicating which eye is selected.

Gaze direction feature measure calculating section 772 calculates the gaze direction feature measure based on the face part three dimensional position information, the three dimensional position of the face reference plane, the gaze feature parameter, the inter-pupil distance, and the pupil selection information generated in use feature selecting section 776.

Figure 16:
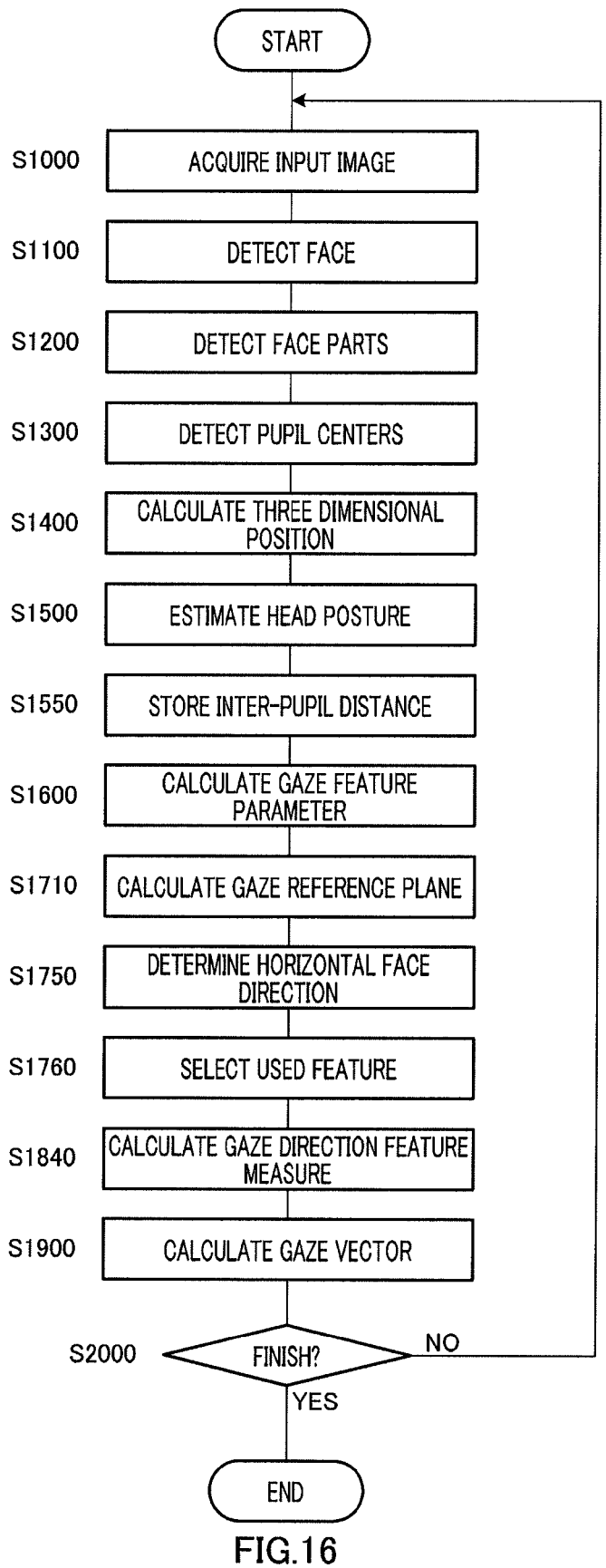
FIG. 16 is a flowchart showing the flow of gaze direction detection processing in a gaze direction detecting apparatus according to Embodiment 5 of the present invention.

FIG. 16 is a flowchart showing the flow of gaze direction detection processing in gaze direction detecting apparatus 700, and is associated with FIG. 12 in Embodiment 4.

The gaze direction detection processing shown in FIG. 16 is the same as in FIG. 12 except that the processing in step S1830 is replaced by the processing in steps S1750 to 1840.

In step S1750, horizontal face direction determining section 774 determines whether the face in the stereo camera coordinate system is directed to the right or left, based on the face front vector acquired in step S1500. Further, horizontal face direction determining section 774 outputs face direction information indicating the determination result, that is, face direction information indicating whether the face is directed toward the right or left, to use feature selecting section 776.

For example, determining whether the face is directed to the right or left in the camera coordinate system is performed as follows. Horizontal face direction determining section 774 acquires the horizontal component of the stereo camera coordinate system representing the face front vector. Here, the left direction is positive when the face is directed to the front. Consequently, when the horizontal component of the face front vector is positive, horizontal face direction determining section 774 determines that the face is directed to the left, and, when the horizontal component of the face front vector is negative, horizontal face direction determining section 774 determines that the face is directed to the right.

Further, the value of the horizontal component of the face front vector can be used as is face direction information. In this case, the face direction information indicates the right or left with positive and negative values. Further, the face direction information may indicate the face direction according to more than two predetermined values such as 0 to indicate that the face is directed to the right and 1 to indicate that the face is directed to the left.

In step S1760, use feature selecting section 776 selects the eye associated with the face direction indicated by the inputted face direction information, with reference to selection information table 775a. Further, use feature selecting section 776 generates pupil selection information indicating the selected eye and outputs the generated pupil selection information to gaze direction feature measure calculating section 772.

Further, the face direction information can be directly made the pupil selection information. In this case, for example, if the face direction information indicates whether the face is directed to the right or left with positive and negative values, the pupil selection information indicates the right eye and left eye with positive and negative values. Further, the pupil selection information may indicate the right eye and left eye with more than two predetermined values such as 0 upon selecting the left eye and 1 upon selecting the right eye.

In step S1840, as in Embodiment 4, gaze direction feature measure calculating section 772 calculates the degree of deviation d that serves as the gaze direction feature measure based on the three dimensional position of the center of the pupil of the eye specified by the pupil selection information. For example, gaze direction feature measure calculating section 772 uses equation 13 exemplified in Embodiment 4 when the pupil selection information specifies the right eye, and uses equation 14 exemplified in Embodiment 4 when the pupil selection information specifies the left eye.

Further, when the horizontal component of the face front vector is 0, upon generating face direction information or pupil selection information and upon determining the calculation method in gaze direction feature measure calculating section 772, it is possible to perform one of the processing associated with the right eye and the processing associated with the left eye.

As described above, according to the present embodiment, it is possible to determine the eye on the front side according to the face direction and perform gaze direction detection using only the eye on the front side. By this means, it is possible to secure the stable detection accuracy upon gaze direction detection. Further, the face direction is determined from the face direction vector which is detected on a regular basis, so that it is possible to continue accurate gaze direction detection.

Further, although a case has been described with the present embodiment where the degree of deviation d is calculated from the distance of the center of the pupil with respect to the gaze reference plane, it is possible to adopt the present embodiment when the degree of deviation d is calculated from the distance of the face part projection point with respect to the gaze reference point as in Embodiment 3. In this case, gaze feature projection section 371 needs to acquire the face part projection point from the eye specified by the pupil selection information.

(Embodiment 6)

A case will be explained with Embodiment 6 where gaze direction detection is performed by weighting the gaze direction feature measure acquired from the right and left eyes according to the face direction.

The reliability of the three dimensional position acquired from the eye on the rear side is low when the face is directed to the right or left greatly, and becomes higher when the direction of the face becomes close to the optical axis direction of the camera. Further, in cases where the subject gazes an extremely close position and therefore a line segment connecting the centers of the right and left pupils is not orthogonal to the gaze reference plane, and where the accuracy of the acquired inter-pupil distance is low, if only one eye is used, the accuracy of gaze direction detection degrades. Therefore, with the present embodiment, gaze direction detection is performed by weighting information acquired from the eye on the rear side and information acquired from the eye on the front side according to the face direction and by using both eyes actively.

Figure 17:
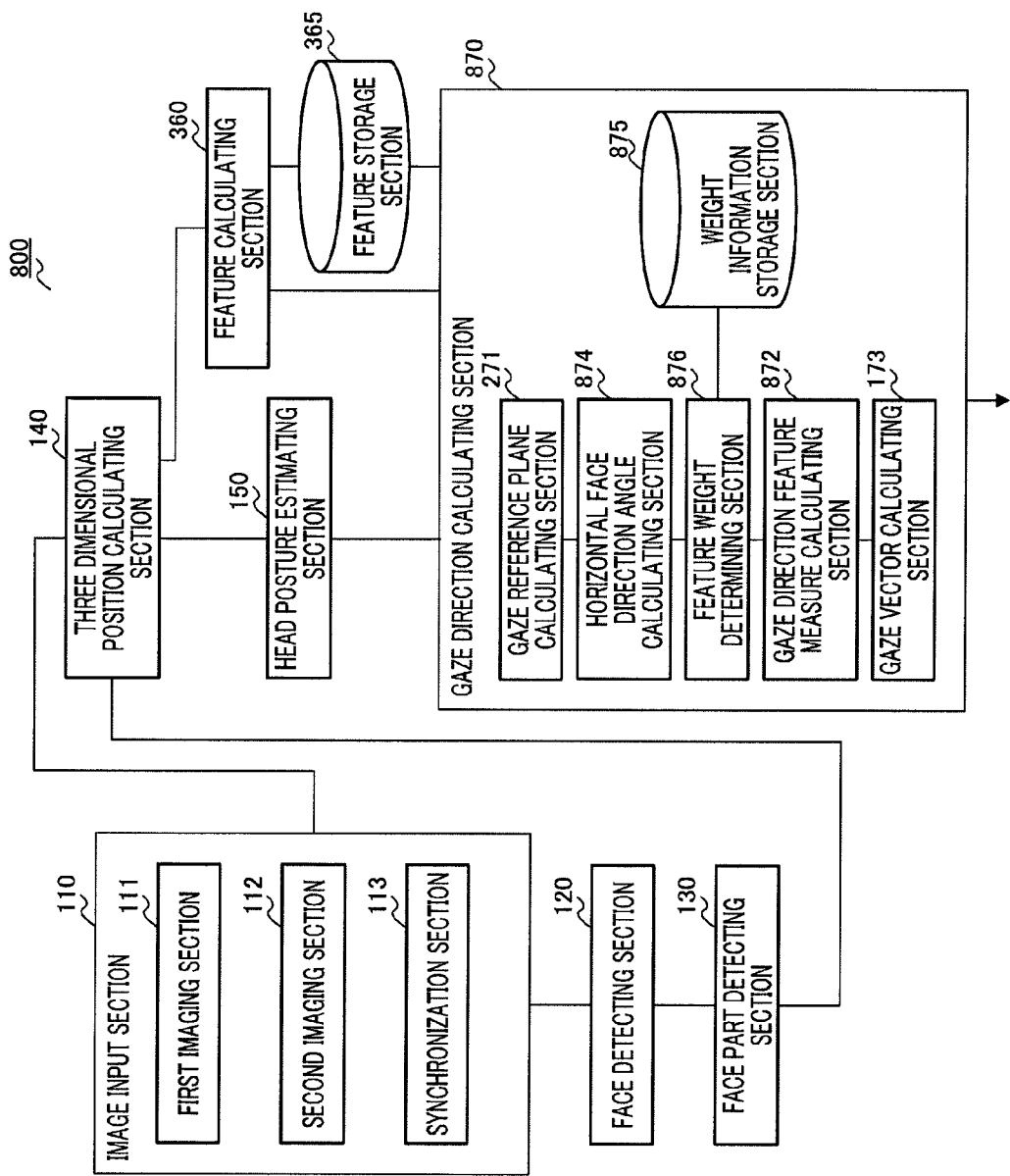
FIG. 17 is a block diagram showing the configuration of a gaze direction detecting apparatus according to Embodiment 6 of the present invention.

FIG. 17 is a block diagram showing the configuration of the gaze direction detecting apparatus according to Embodiment 5 of the present invention, and is associated with FIG. 14 in Embodiment 5.

In FIG. 17, gaze direction detecting apparatus 800 of the present embodiment provides gaze direction calculating apparatus 870 instead of gaze direction calculating section 770 shown in FIG. 14. Gaze direction calculating section 870 provides horizontal face direction angle calculating section 874, weight information storage section 875, feature weight determining section 876 and gaze direction feature measure calculating section 872 instead of horizontal face direction determining section 774, selection information storage section 775, use feature selecting section 776 and gaze direction measure calculating section 772 shown in FIG. 14.

In gaze direction calculating section 870, horizontal face direction angle calculating section 874 calculates the angle of the face with respect to the optical axis of the camera in the horizontal direction, from the face front vector acquired in head posture estimating section 150, as the horizontal face direction angle.

Weight information storage section 875 stores weight information. Weight information associates in advance horizontal face direction angles with values that depends on the balance of the reliability of information acquired from the right and left eyes and that serve as weight values (hereinafter "left eye weight values") to be weighted on information acquired from the left eye. Weight information may be given in, for example, a table format in which left eye weight coefficients are described in association with discrete values of the horizontal face direction angle or in a functional format in which the left eye weight coefficients are determined as the function of the horizontal face direction angle.

FIG. 18 illustrates an example of content of weight information in a table format.

As shown in FIG. 18, table-format weight information 876a describes the left eye weight coefficients as values that gradually decrease from one to zero according to an increase of the horizontal face direction angle. That is, when the direction of the face becomes close to the right, the left eye weight coefficient increases, and, when the direction of the face becomes close to the left, the left eye weight coefficient decreases. The reason is that, when the direction of the face becomes close to the right, the reliability of information acquired from the right eye degrades, and, when the direction of the face becomes close to the left, the reliability of information acquired from the left eye degrades. As shown in FIG. 18, when the face is directed to the right or left greatly, weight of the eye on the rear side is made 0, and, when the direction of the face is close to the front (i.e., the optical axis direction of the camera), it is possible to reduce processing loads by applying the same weights to the right and left eyes.

Figure 19:
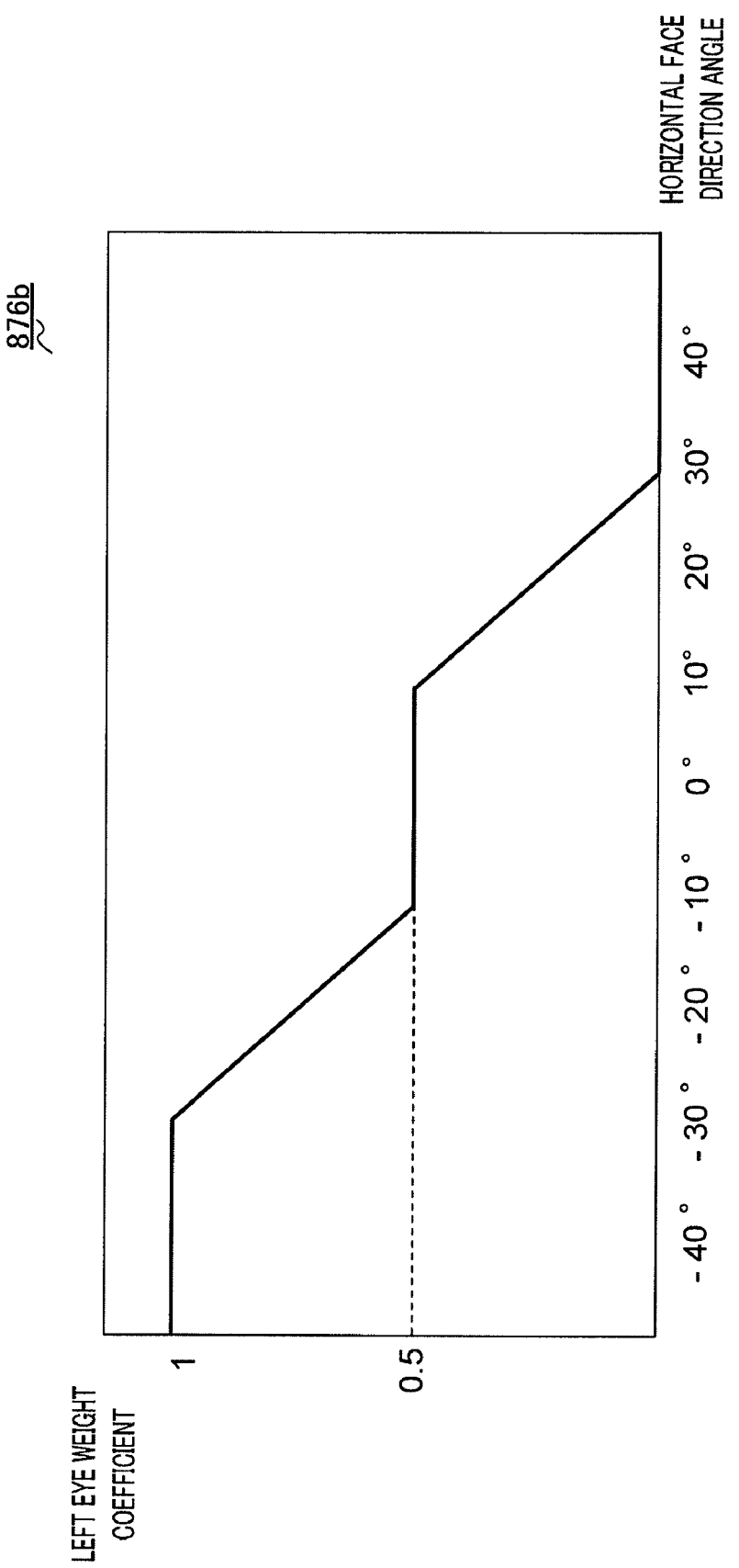
FIG. 19 illustrates another example of content of weight information according to Embodiment 6 of the present invention.

FIG. 19 illustrates an example of content of weight information in a functional format.

As shown in FIG. 19, functional-format weight information 876b also defines the left eye weight coefficient with continuing values that gradually decrease from 1 to 0 according to an increase of the horizontal face direction angle. When functional-format weight information 876b is used, it is possible to determine the left eye weight coefficient more accurately compared to a case where table-format weight information 876a is used.

Feature weight determining section 876 in FIG. 17 acquires the left eye weight coefficient from the horizontal face direction angle calculated in horizontal face direction angle calculating section 874 using weight information. Further, feature weight determining section 876 outputs to gaze direction feature measure calculating section 872 the acquired left eye weight coefficient as the feature weight information indicating the weight for use upon calculating the degree of deviation that serves as the gaze direction feature measure.

Gaze direction feature measure calculating section 872 calculates the gaze direction feature measure based on the face part three dimensional position information, the three dimensional position of the gaze reference plane, the gaze feature parameter, the inter-pupil distance, and the feature weight information acquired in feature weight determining section 876.

Figure 20:
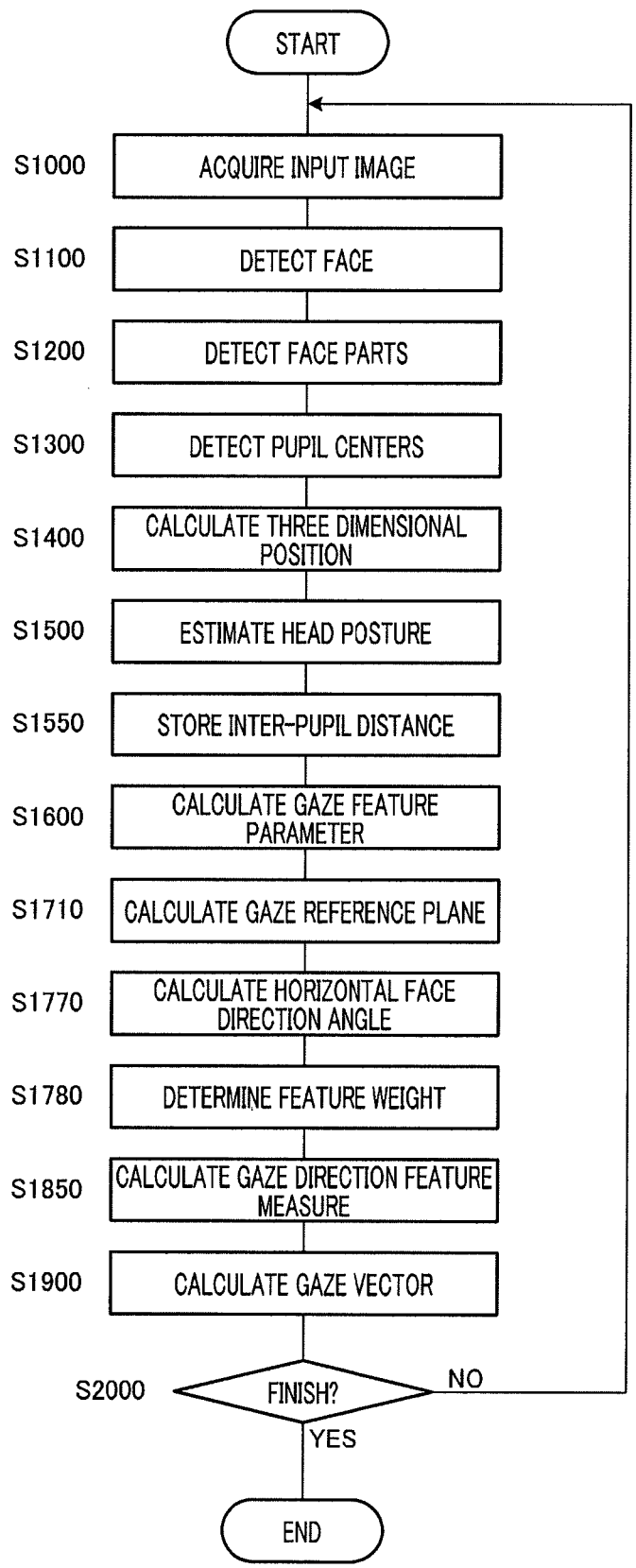
FIG. 20 is a flowchart showing the flow of gaze direction detection processing in a gaze direction detecting apparatus according to Embodiment 6 of the present invention.

FIG. 20 is a flowchart showing the flow of gaze direction detection processing in gaze direction detecting apparatus 800, and is associated with FIG. 16 in Embodiment 5.

The processing shown in FIG. 20 are the same as in FIG. 16 except that the processing in steps S1750 to 1840 are replaced by the processing in steps S1770 to 1850.

In step S1770, horizontal face direction angle calculating section 874 calculates an angle of the horizontal component of the face direction with respect to the optical axis direction of the camera, as the horizontal face direction angle, based on the face front vector acquired in step S1500, and outputs the calculated horizontal face direction angle to feature weight determining section 876.

For example, the calculation of the horizontal face direction angle is performed as follows. When the horizontal component, vertical component and optical axis component of the face front vector in the stereo camera coordinate system are $(X_{fc}, Y_{fc}, Z_{fc})$, horizontal face direction angle calculating section 874 calculates horizontal face direction angle $\theta_h$ using, for example, following equation 15.

(Equation 15)

$$\theta_h = \sin^{-1}\left(\frac{X_{fc}}{\sqrt{X_{fc}^2 + Z_{fc}^2}}\right) \quad [15]$$

In step S1780, feature weight determining section 876 determines the left eye weight coefficient associated with the inputted horizontal face direction angle based on the weight information stored in weight information storage section 875, and calculates a weight coefficient (hereinafter "right eye weight coefficient") to be multiplied by information acquired form the right eye using the determined left eye weight coefficient. Further, feature weight determining section 876 outputs the left eye weight coefficient and right eye weight coefficient, as feature weight information, to gaze direction feature measure calculating section 872.

When the left eye weight coefficient is $W_l$, feature weight determining section 876 calculates right eye weight coefficient $W_r$ using, for example, following equation 16.

[16]

$$W_r = 1 - W_l \quad \text{(Equation 16)}$$

Further, gaze direction feature measure calculating section 872 may calculate the right eye weight coefficient using equation 16. In this case, feature weight measure determining section 876 outputs only the left eye weight coefficient to gaze direction feature measure calculating section 872 as feature weight information.

In step S1850, gaze direction feature measure calculating section 872 performs weighting for information acquired from the three dimensional positions of the centers of the right and left pupils according to the feature weight information, to calculate the degree of deviation d that serves as the gaze direction feature measure.

Weighting for the information acquired from the three dimensional positions of the centers of the right and left pupils is performed as follows, for example. If the components of face part vector 611 are (a, b, c), the coordinates of gaze direction reference point Fc are $(x_f, y_f, z_f)$, the coordinates of the center of the pupil of the right eye are $(x_r, y_r, z_r)$, and the coordinates of the center of the pupil of the left eye are $(x_l, y_l, z_l)$, for example, gaze direction feature measure calculating section 872 calculates the degree of deviation $d_c$ upon using the right eye by following equation 17 and calculates the degree of deviation $d_l$ upon using the left eye by following equation 18.

(Equation 17)

$$d_r = \frac{|a(x_r - x_f) + b(y_r - y_f) + c(z_r - z_f)|}{\sqrt{a^2 + b^2 + c^2}} - 0.5 L_{eye} \quad [17]$$

(Equation 18)

$$d_l = -\left(\frac{|a(x_l - x_f) + b(y_l - y_f) + c(z_l - z_f)|}{\sqrt{a^2 + b^2 + c^2}} - 0.5 L_{eye}\right) \quad [18]$$

Further, by calculating the sum of the value acquired by multiplying the calculated degree of deviation $d_c$ by right eye weight coefficient $W_c$ and the value acquired by multiplying the calculated degree of deviation $d_l$ by left eye weight coefficient $W_l$, that is, by using following equation 19, gaze direction feature measure calculating section 872 calculates the degree of deviation d that serves as the final gaze direction feature measure.

[19]

$$d = W_r d_r + W_l d_l \quad \text{(Equation 19)}$$

Further, in the weighting, it is possible to calculate angle θ formed by the gaze vector and the face front vector using the degrees of deviations calculated from the right and left eyes individually, and weight the weight coefficients associated with two calculated values, respectively.

To be more specific, for example, first, gaze direction feature measure calculating section 872 calculates the degree of deviation $d_c$ upon using the right eye and the degree of deviation $d_l$ upon using the left eye, and outputs the calculation results, right eye weight coefficient $W_c$ and left eye weight coefficient $W_l$ to gaze vector calculating section 173. Next, gaze vector calculating section 173 calculates angle $\theta_r$ formed by the gaze vector and face front vector upon using the right eye and angle $\theta_l$ formed by the gaze vector and face front vector upon using the left eye by following equations 20 and 21, using eyeball radius r and the degrees of deviations $d_r$ and $d_l$.

(Equation 20)

$$\theta_r = \sin^{-1}\left(\frac{d_r}{r}\right) \quad [20]$$

(Equation 21)

$$\theta_l = \sin^{-1}\left(\frac{d_l}{r}\right) \quad [21]$$

Further, by calculating the sum of the value acquired by multiplying calculated angle $\theta_r$ by right eye weight coefficient $W_r$ and the value acquired by multiplying calculated angle and $\theta_l$ by left eye weight coefficient $W_l$, that is, by using following equation 22, gaze vector calculating section 173 calculates the degree of deviation d that serves as the final gaze direction feature measure.

[22]

$$\theta = W_r\theta_r + W_l\theta_l \quad \text{(Equation 22)}$$

As described above, according to the present embodiment, weighting is performed according to the reliability of information acquired from the right and left eyes, and gaze direction detection is performed using both eyes actively. By this means, it is possible to stabilize the accuracy of gaze direction detection.

Here, by analyzing in advance the relationships between the accuracy of detecting the three dimensional position of the center of the pupil and the imaging condition, the accuracy of detecting the inter-pupil distance and the horizontal face direction angle by experiments, and, by calculating from the analysis results the weight which best stabilizes the accuracy of gaze direction detection per horizontal face direction angle, so that it is possible to further stabilize the accuracy of gaze direction detection. Further, it is equally possible to prepare weight information of different content depending on the imaging condition and use the unique weight information depending on the imaging condition.

Further, although a case has been described with the present embodiment where the degree of deviation d is calculated from the distance between the gaze reference plane and the center of the pupil, it is equally possible to adopt the present embodiment in a case where the degree of deviation d is calculated from the distance between the gaze direction reference point and the face part projection point as in Embodiment 3. In this case, gaze feature projection section 371 needs to acquire the face part projection points from the right and left eyes, and gaze direction feature measure calculating section 372 needs to calculate the degree of deviations from both eyes, respectively, and then perform weighting according to the feature weight information.

Although cases have been explained with the above-described embodiments where these embodiments are applied to a warning apparatus that warns the car driver of the risks of accidents, it is equally possible to apply these embodiments to other various apparatuses that perform processing based on a person's gaze direction.

For example, these apparatuses include information presenting devices such as televisions and acoustic speakers, safety state monitoring devices such as monitoring cameras, image storage devices such as still cameras and video cameras, life support devices such as robots, and playing devices such as video games and play equipment. Further, for example, the apparatuses include image storage apparatuses that input and store images the car driver is assumed to look at, neighboring information assessing apparatuses for robots to assess the condition of users or the condition of the robots themselves, game condition updating apparatuses to change the condition of game content of video games, and medical devices to examine the movement of the eyes.

Further, the subject targeted for gaze direction detection is not limited to human. It is possible to apply the present invention to animals which have two face parts that are located laterally symmetrically with respect to the center of the face and in which the centers of the pupils can be detected, to detect the gaze direction.

The disclosure of Japanese Patent Application No. 2006-194892, filed on Jul. 14, 2006, including the specification, drawings and abstract, is incorporated herein by reference in its entirety.

INDUSTRIAL APPLICABILITY

The gaze direction detecting apparatus and gaze direction detecting method according to the present invention are useful as a gaze direction detecting apparatus and gaze direction detecting method for acquiring an accurate gaze direction detection result without having to perform calibration on a per subject basis. To be more specific, the gaze direction detecting apparatus is useful as an information terminal such as personal computer, OA (Office Automation) device and mobile phone, and an information providing apparatus equipped with transportation means such as car, airplane, ship and train. Further, it is possible to adopt the gaze direction detecting apparatus as information input apparatus for a monitoring apparatus, a warning apparatus, a robot, an audio and video playback apparatus and the like.

The invention claimed is:

1. A gaze direction detecting apparatus that detects a gaze direction of a subject based on an image including at least part of the subject, comprising:
   a feature position calculator that extracts position information of a left pupil of the subject and position information of a right pupil of the subject from the image, and calculates position information of a first middle point between the position information of the left pupil and the position information of the right pupil;
   a reference position calculator that extracts facial parts symmetrically existing in the subject in the image and calculates position information of a second middle point between position information of one facial part and position information of an other facial part, the one facial part and the other facial part being different than the left pupil and the right pupil; and
   a gaze direction calculator that calculates a first gaze direction of the subject based on the position information of the first middle point, the position information of the second middle point, and a predetermined radius of an eyeball.

2. The gaze direction detecting apparatus according to claim 1, wherein the gaze direction calculator calculates the first gaze direction based on a deviation between elements of a direction of a straight line through one of the left pupil and the right pupil, and the one facial part and the other facial part, a deviation between the position information of the first middle point and the position information of the second middle point information, and the predetermined radius of the eyeball.

3. The gaze direction detecting apparatus according to claim 1, further comprising:
   a face direction determiner that determines whether a front face of the subject is directed toward one of a right side and a left side of the image; and
   a feature selector that selects a selected pupil that is closer to the gaze direction detecting apparatus from among the left pupil and the right pupil based on a determination of whether the front face is directed toward the one of the right side and the left side by the face direction determiner,
   wherein after calculating the first gaze direction, the gaze direction calculator calculates a second gaze direction of the subject based on a half value of a distance between the left pupil and the right pupil, position information of the selected pupil among the left pupil and the right pupil, the position information of the second middle point, and the predetermined radius of the eyeball.

4. The gaze direction detecting apparatus according to claim 1, further comprising:
   a face direction angle calculator that calculates an angle of horizontal direction of a front face of the subject; and a feature weight determiner that determines a weight coefficient of each of the left pupil and the right pupil based on the angle calculated by the face direction angle calculator, and wherein after calculating the first gaze direction, the gaze direction calculator calculates a second gaze direction of the subject based on a half value of a distance between the left pupil and the right pupil, the weight coefficient of each of the left pupil and the right pupil, the position information of the left pupil, the position information of the right pupil, the position information of the second middle point, and the predetermined radius of the eyeball.

5. A gaze direction detecting method for detecting a gaze direction of a subject based on an image including at least part of the subject, comprising:

extracting position information of a left pupil of the subject and position information of a right pupil of the subject from the image;

calculating position information of a first middle point between the position information of the left pupil and the position information of the right pupil;

extracting facial parts symmetrically existing in the subject in the image;

calculating position information of a second middle point between position information of one facial part and position information of an other facial part, the one facial part and the other facial part being different than the left pupil and the right pupil; and calculating, by a processor, a first gaze direction of the subject based on the position information of the first middle point, the position information of the second middle point, and a predetermined radius of an eyeball.

* * * * *